United States Patent
Serokosz et al.

(10) Patent No.: US 11,413,028 B2
(45) Date of Patent: Aug. 16, 2022

(54) SCREW-BASED RETRACTOR HAVING ARMS WITH PLURAL DISCRETE SELECTIVELY LOCKABLE POSITIONS

(71) Applicant: SPINE WAVE, INC., Shelton, CT (US)

(72) Inventors: Mark Serokosz, New Fairfield, CT (US); Eugene Avidano, Stratford, CT (US); Dylan Freund, Southbury, CT (US); David Boisvert, Southington, CT (US)

(73) Assignee: SPINE WAVE, INC., Shelton, CT (US)

( * ) Notice: Subject to any disclaimer, the term of this patent is extended or adjusted under 35 U.S.C. 154(b) by 396 days.

(21) Appl. No.: 16/443,927

(22) Filed: Jun. 18, 2019

(65) Prior Publication Data

US 2019/0298327 A1 Oct. 3, 2019

Related U.S. Application Data

(63) Continuation-in-part of application No. 16/023,481, filed on Jun. 29, 2018, now Pat. No. 10,363,022.
(Continued)

(51) Int. Cl.
*A61B 17/02* (2006.01)
*A61B 17/86* (2006.01)

(52) U.S. Cl.
CPC ........ *A61B 17/025* (2013.01); *A61B 17/0206* (2013.01); *A61B 17/86* (2013.01); *A61B 2017/0256* (2013.01)

(58) Field of Classification Search
CPC ... A61B 17/025; A61B 17/0206; A61B 17/86; A61B 2017/0256
(Continued)

(56) References Cited

U.S. PATENT DOCUMENTS

| | | |
|---|---|---|
| 1,371,882 A | 3/1921 | Ferguson et al. |
| 3,749,088 A | 7/1973 | Kohlmann |

(Continued)

FOREIGN PATENT DOCUMENTS

| | | |
|---|---|---|
| EP | 2705799 | 12/2014 |
| EP | 3100687 | 7/2016 |

(Continued)

*Primary Examiner* — Nicholas J Plionis
*Assistant Examiner* — David C Comstock
(74) *Attorney, Agent, or Firm* — Hoffmann & Baron, LLP

(57) ABSTRACT

A screw-based retractor comprises an elongate rack having a rack axis, a plurality of arms slidably supported for translational movement on the rack, and a plurality of blades, one each supported by a respective arm at a distal portion thereof. At least one of the arms includes at its distal portion a blade releasably attached thereto. Such at least one arm comprises a plurality of links each of which is configured to allow the blade supported by such arm to be moved in plural incrementally discrete positions with each such discrete position being selectively lockable. The blade may have a fixed or variable length. Such blade may be attached to a blade receptacle movably attached to the at least one arm in a manner to provide articulation of the blade receptacle and hence the attached blade about an articulation point spaced from and not located on such arm.

30 Claims, 31 Drawing Sheets

Related U.S. Application Data

(60) Provisional application No. 62/573,869, filed on Oct. 18, 2017.

(58) Field of Classification Search
USPC ....... 600/210, 213, 215, 225, 227, 228, 229; 606/264
See application file for complete search history.

(56) References Cited

U.S. PATENT DOCUMENTS

| | | | |
|---|---|---|---|
| 4,616,635 A | 10/1986 | Caspar et al. | |
| 4,662,771 A | 5/1987 | Roe et al. | |
| 4,690,132 A | 9/1987 | Bayer et al. | |
| 5,807,378 A | 9/1998 | Jensen et al. | |
| 6,083,225 A * | 7/2000 | Winslow | A61F 2/446 606/86 A |
| 6,599,240 B2 | 7/2003 | Puchovsky et al. | |
| 6,869,398 B2 | 3/2005 | Obenchain et al. | |
| 7,588,578 B2 | 9/2009 | Triplett et al. | |
| 7,618,424 B2 | 11/2009 | Wilcox et al. | |
| 7,758,584 B2 | 7/2010 | Bankoski et al. | |
| 8,100,828 B2 | 1/2012 | Frey et al. | |
| 8,357,184 B2 | 1/2013 | Woolley et al. | |
| 8,435,269 B2 | 5/2013 | Woolley et al. | |
| 8,535,320 B2 | 9/2013 | Woolley et al. | |
| 8,636,655 B1 | 1/2014 | Childs | |
| 8,679,129 B2 | 3/2014 | Sorrenti et al. | |
| 8,834,485 B2 | 9/2014 | Kave | |
| 9,050,146 B2 | 6/2015 | Woolley et al. | |
| 9,216,016 B2 | 12/2015 | Fiechter et al. | |
| 9,307,972 B2 | 4/2016 | Lovell et al. | |
| 9,414,828 B2 | 8/2016 | Abidin et al. | |
| 9,554,833 B2 | 1/2017 | Woolley et al. | |
| 9,572,560 B2 | 2/2017 | Mast et al. | |
| 9,675,337 B2 | 6/2017 | Gorek et al. | |
| 9,700,293 B2 | 7/2017 | Cryder et al. | |
| 9,795,370 B2 | 10/2017 | O'Connell et al. | |
| 9,907,582 B1 * | 3/2018 | Olea | A61B 17/60 |
| 9,962,147 B2 | 5/2018 | O'Connell et al. | |
| 2002/0198526 A1 | 12/2002 | Shaolian et al. | |
| 2003/0149341 A1 | 8/2003 | Clifton | |
| 2004/0138660 A1 | 7/2004 | Serhan | |
| 2007/0161865 A1 | 7/2007 | Fakhrai | |
| 2007/0173745 A1 | 7/2007 | Diederich et al. | |
| 2008/0255567 A1 | 10/2008 | Accordino | |
| 2008/0262318 A1 | 10/2008 | Gorek et al. | |
| 2009/0018401 A1 | 1/2009 | Kim | |
| 2009/0203969 A1 * | 8/2009 | Cohen | A61B 17/0206 600/245 |
| 2009/0221878 A1 | 9/2009 | Gorek | |
| 2009/0222044 A1 | 9/2009 | Gorek | |
| 2011/0130634 A1 * | 6/2011 | Solitario, Jr | A61B 17/3421 600/231 |
| 2011/0172494 A1 | 7/2011 | Bass et al. | |
| 2011/0295328 A1 | 12/2011 | Woolley et al. | |
| 2011/0301422 A1 | 12/2011 | Woolley et al. | |
| 2012/0296171 A1 * | 11/2012 | Lovell | A61B 17/0218 600/213 |
| 2013/0310942 A1 | 11/2013 | Abdou | |
| 2014/0012269 A1 | 1/2014 | Bass | |
| 2014/0031874 A1 | 1/2014 | Kucharzyk et al. | |
| 2014/0066718 A1 * | 3/2014 | Fiechter | A61B 17/7077 600/214 |
| 2014/0148652 A1 | 5/2014 | Weiman | |
| 2015/0018628 A1 | 1/2015 | Friedrich et al. | |
| 2015/0164569 A1 | 6/2015 | Reitblat et al. | |
| 2015/0230787 A1 | 8/2015 | Friedrich et al. | |
| 2016/0030030 A1 | 2/2016 | Bass | |
| 2016/0074029 A1 * | 3/2016 | O'Connell | A61B 17/025 600/213 |
| 2016/0192922 A1 | 7/2016 | Friedrich et al. | |
| 2016/0212757 A1 * | 7/2016 | Jung | H04W 72/048 |
| 2017/0086812 A1 | 3/2017 | Mast et al. | |
| 2017/0105770 A1 | 4/2017 | Woolley et al. | |
| 2017/0143323 A1 | 5/2017 | Cryder et al. | |
| 2017/0172556 A1 | 6/2017 | Bass et al. | |
| 2017/0196597 A1 | 7/2017 | Corbin et al. | |
| 2019/0021715 A1 * | 1/2019 | O'Connell | A61B 17/0206 |

FOREIGN PATENT DOCUMENTS

| | | |
|---|---|---|
| GB | 2528416 | 1/2016 |
| WO | 2006/017886 | 2/2006 |
| WO | 2016/007412 | 1/2016 |
| WO | 2016/025020 | 2/2016 |
| WO | 2017/031287 | 2/2017 |

* cited by examiner

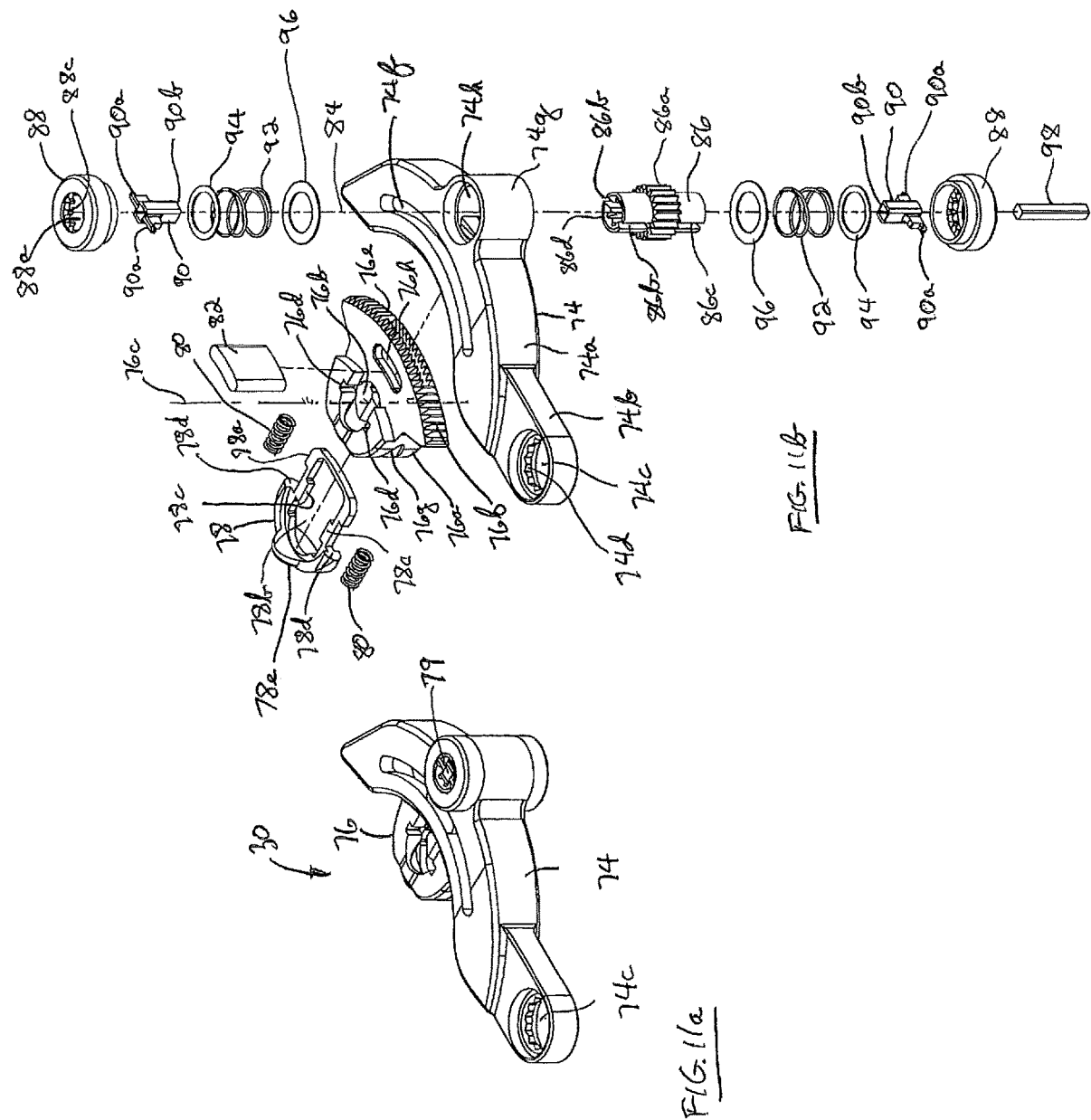

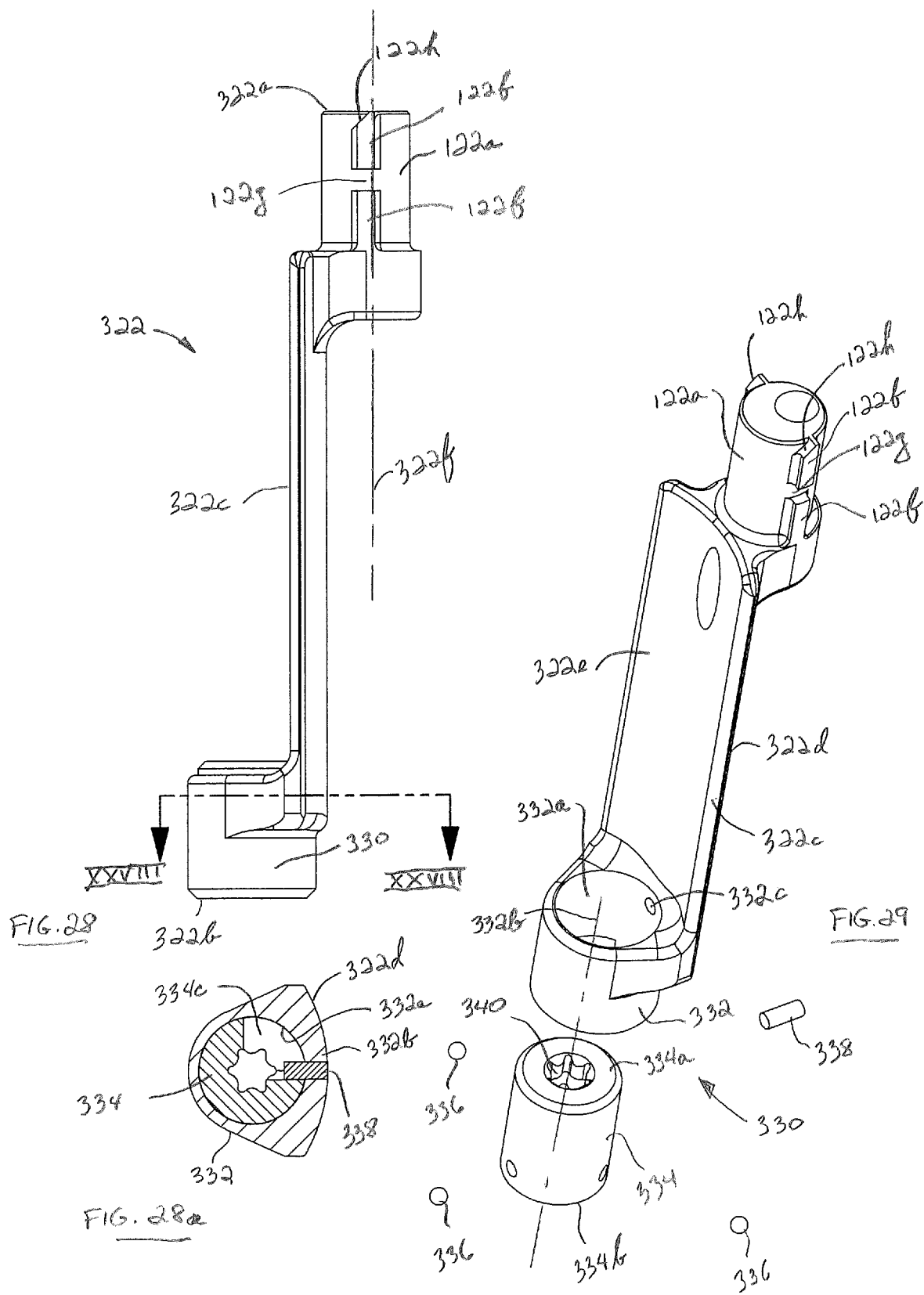

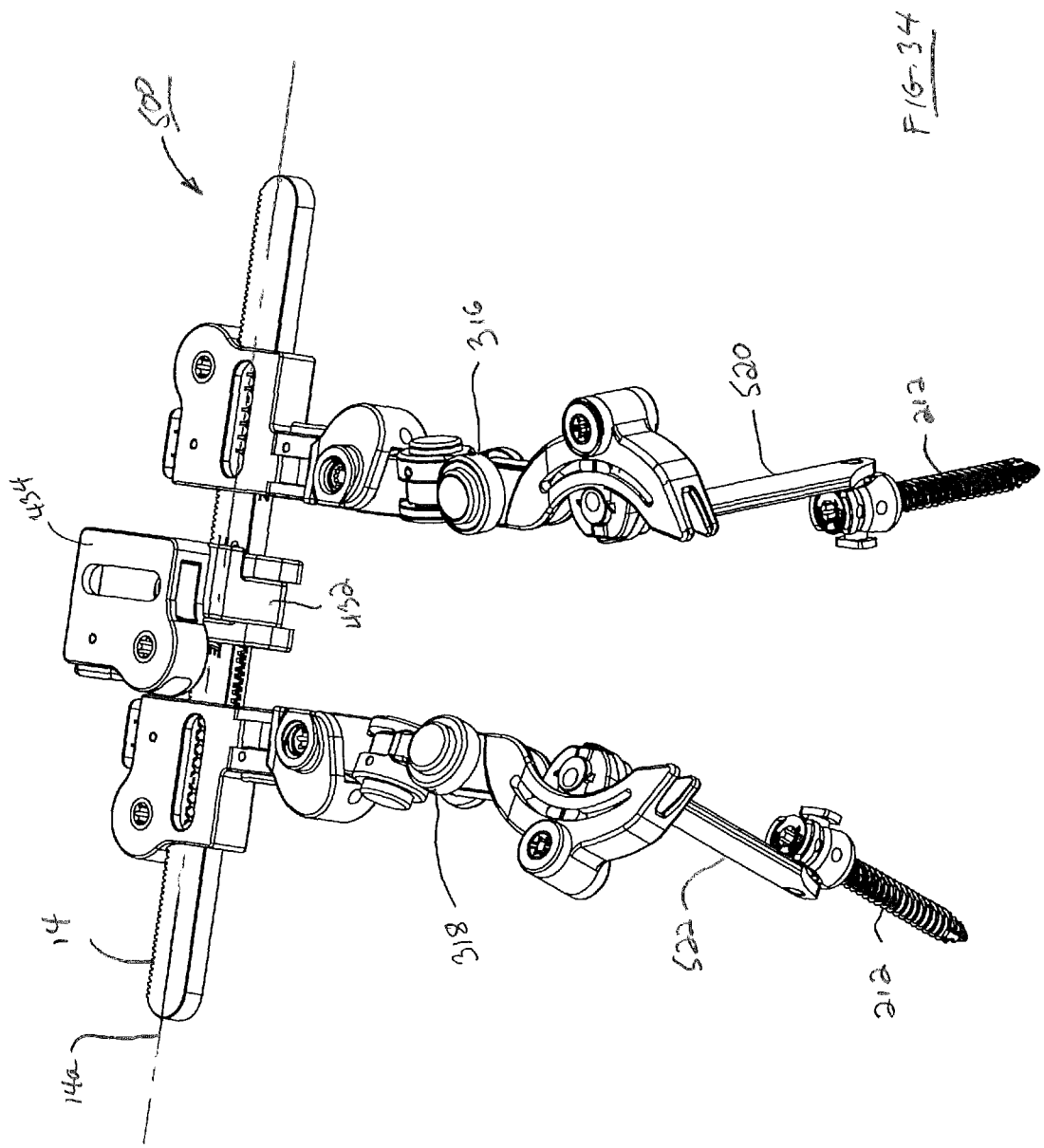

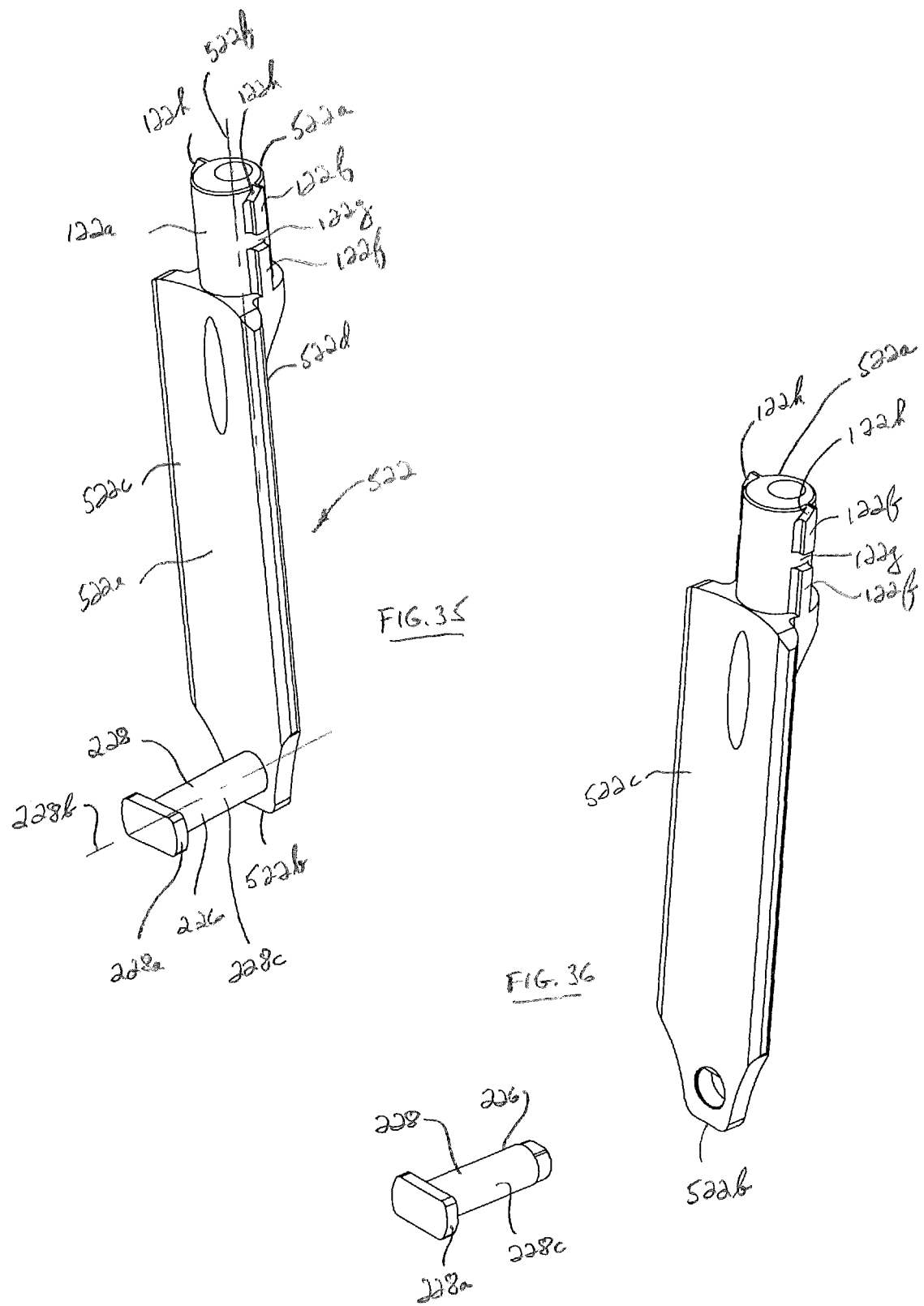

SCREW-BASED RETRACTOR HAVING ARMS WITH PLURAL DISCRETE SELECTIVELY LOCKABLE POSITIONS

CROSS-REFERENCES TO RELATED APPLICATIONS

This application is a continuation-in-part application of U.S. application Ser. No. 16/023,481, filed Jun. 29, 2018, now allowed, which claims the benefit of U.S. Provisional Patent Application No. 62/573,869, filed Oct. 18, 2017, which is incorporated herein by reference in its entirety.

FIELD OF THE INVENTION

The subject invention relates generally to the field of retractors for retracting bodily tissue during surgery and more particularly to a screw-based retractor for use in spinal surgery.

BACKGROUND OF THE INVENTION

Retractors are commonly used in surgical procedures to separate and expand an incision to access the surgical site and to minimize trauma to the patient. While there are many styles, shapes and sizes of retractors, the typical retractor used in spinal surgery comprises a plurality of retractable blades, which may include two to four or more blades that are introduced through the surgical incision to form a protected corridor to the surgical site. Various mechanisms are provided to move one or more blades in different directions so as to expand the incision and to hold the blades in the expanded position. One factor in the surgeon's decision as to the type of retractor used is the control of the blade movement. Blades are often configured to not only expand outwardly so as to expand the corridor but also to pivot or toe at their distal ends so as to increase the opening of the corridor adjacent the surgical site. In addition, the size of the retractor is often of consequence, with the surgeon typically seeking to minimize the overall footprint of the retractor for ease of handling, placement and use during surgery.

One form of a retractor that has emerged primarily in minimally invasive spine surgery is a screw-based retractor that combines the functions of both a retractor and a distractor/compressor. In such a screw-based retractor, a pair of retractor blades may be attached to the patient's anatomy by connecting each blade to a pedicle screw that is anchored to respective vertebra of the patient. Moving the blades relatively away from each other not only provides retraction of surrounding soft tissue, but also distracts the respective vertebra for subsequent fixation. Compression may be effected by moving the blades relatively toward each other. Examples of such screw-based retractors are described in U.S. Pat. No. 9,216,016, entitled "Surgical Device for Minimally Invasive Spinal Fusion and Surgical System Comprising the Same", issued to Fiechter et al. on Dec. 22, 2015, and U.S. Pat. No. 9,414,828, entitled "Integrated Retractor-Distractor System for Use with Modular Bone Screws", issued to Abidin et al. on Aug. 16, 2016. While such screw-based retractor systems exhibit certain improved features, a screw-based retractor having further degrees of freedom for enhanced user applicability is desirable.

SUMMARY OF THE INVENTION

It is an object of the invention to provide an improved retractor for use during surgery, particularly spinal surgery. It is a more particular object of the invention to provide a screw-based retractor that allows the user more freedom in the placement of pedicle screws and to have an instrument with plural selectively lockable discrete positions when patient anatomy may otherwise hinder a user from distracting vertebral bodies where blades are attached to the pedicle screws.

DESCRIPTION OF THE FIGURES

FIG. 10b is a side elevation view of the hex button of FIG. 10a.

FIG. 11a is a top perspective view of the blade arm assembly of the retractor arm.

FIG. 11b is an exploded view of the blade arm assembly of FIG. 11a.

FIG. 14a is a top perspective view of a retractor blade of the retractor embodiment shown in FIG. 1, with the blade being in a fully expanded condition.

FIG. 14b is a top perspective exploded view of the retractor blade of FIG. 14a.

FIG. 14c is a side elevation view of the retractor blade of FIG. 14a.

FIG. 14d is a front elevation view of the retractor blade of FIG. 14a.

FIG. 14e is a top plan view of the retractor blade of FIG. 14a.

FIG. 14f is a top perspective view of the retractor blade of the retractor embodiment shown in FIG. 1, with the blade being in a fully contracted condition.

Figure 16:
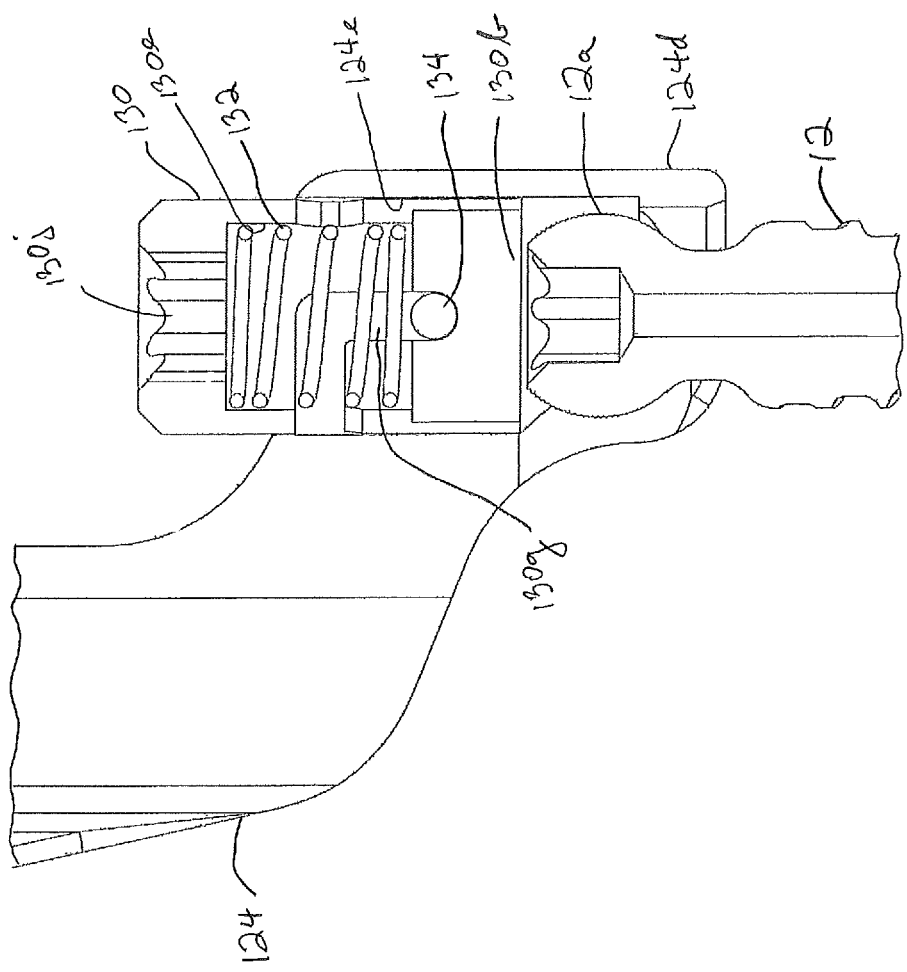
FIG. 16 is a partial cross-sectional view of the distal end of the retractor blade of the retractor arrangement of FIG. 1 showing the retainer of FIG. 15 normally biased to a position to receive the head of the bone screw in the bone screw attachment member.
Figure 17:
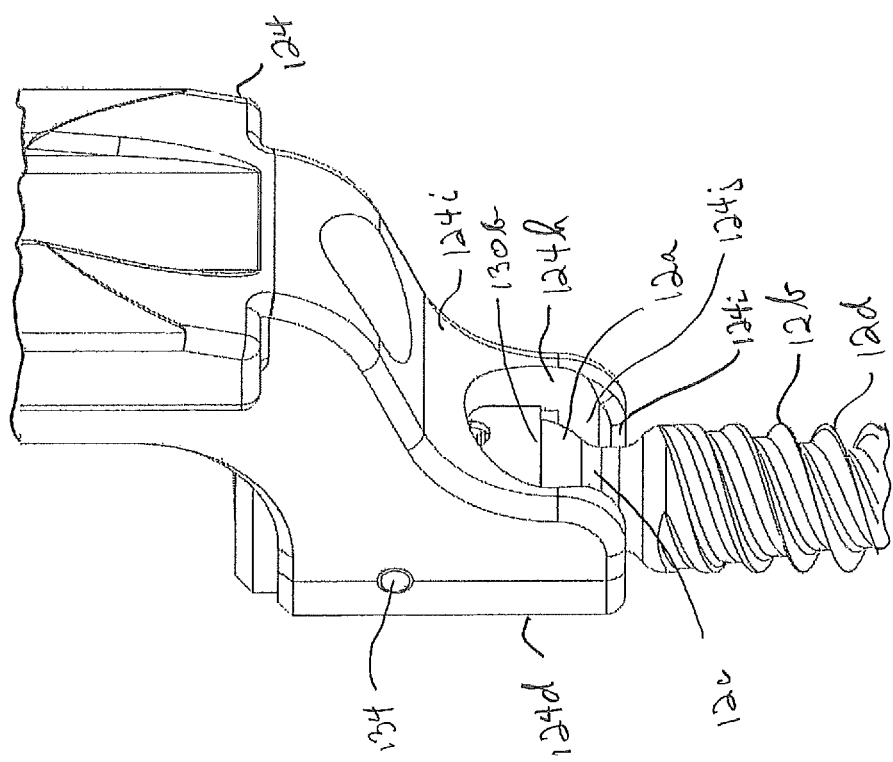

FIG. 17 is a partial rearward perspective view of an entrance port of the bone screw attachment member of FIG. 16 with the head of the bone screw received therein.

Figure 18:
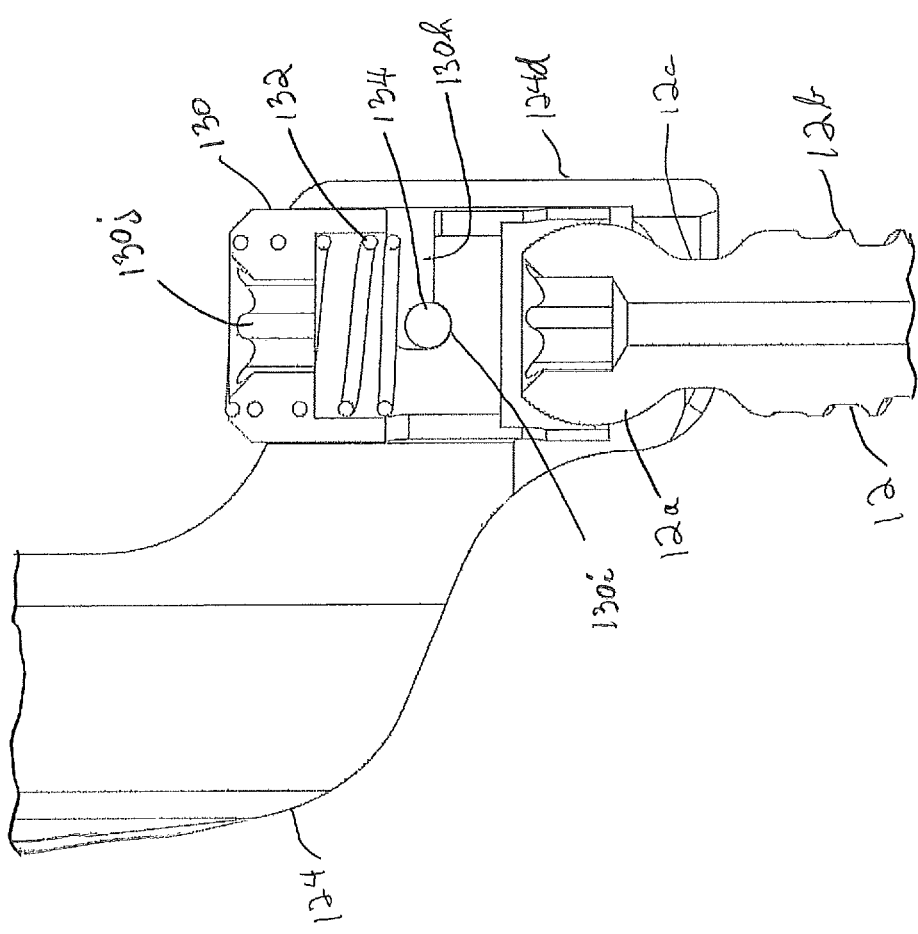

FIG. 18 is the partial cross-sectional view of FIG. 16 with the retainer moved to a position releasably holding the head of the bone screw.

Figure 1:
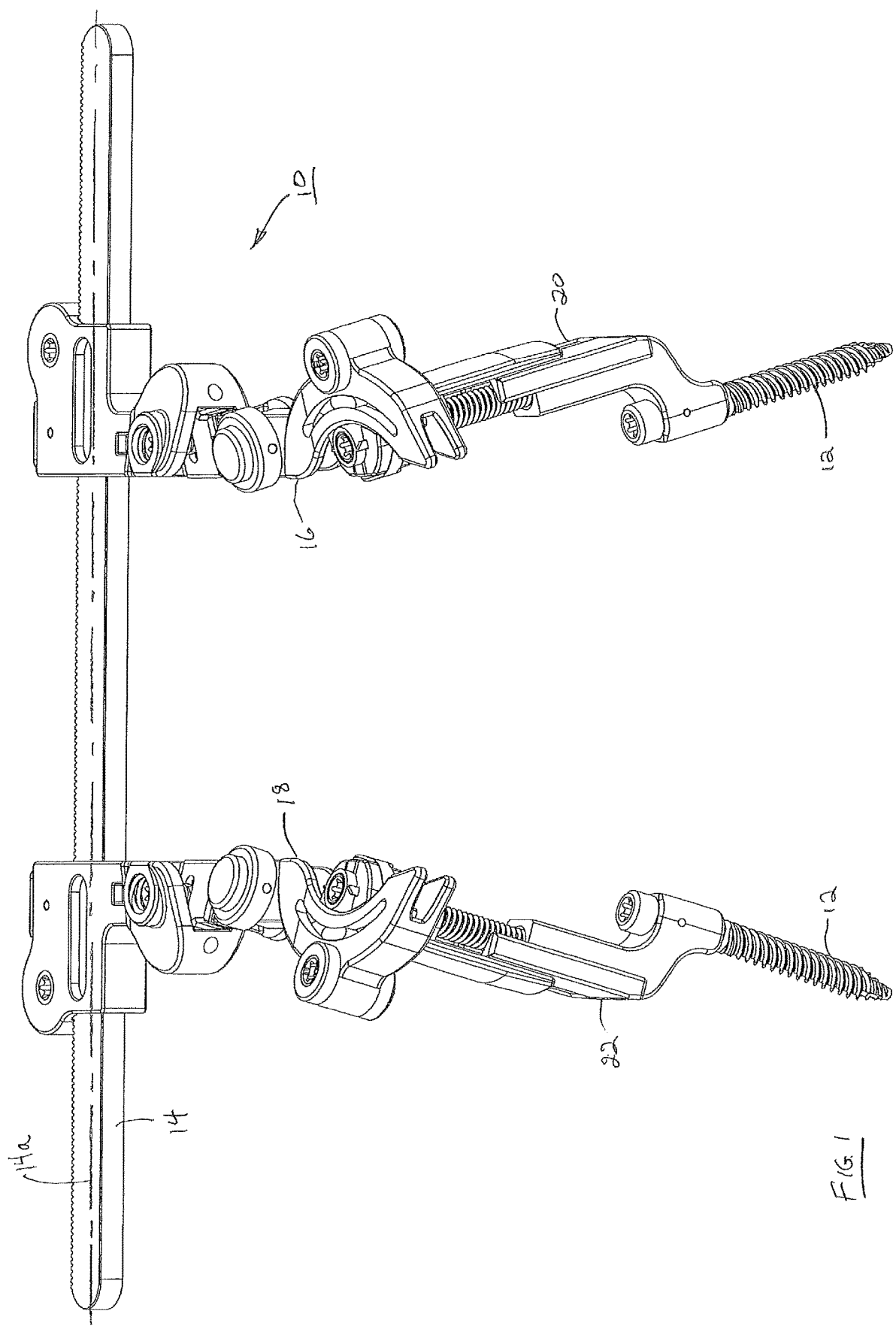
FIG. 1 is a top perspective of a screw-based retractor for use during spinal surgery in accordance with one embodiment of the present invention.
Figure 19:
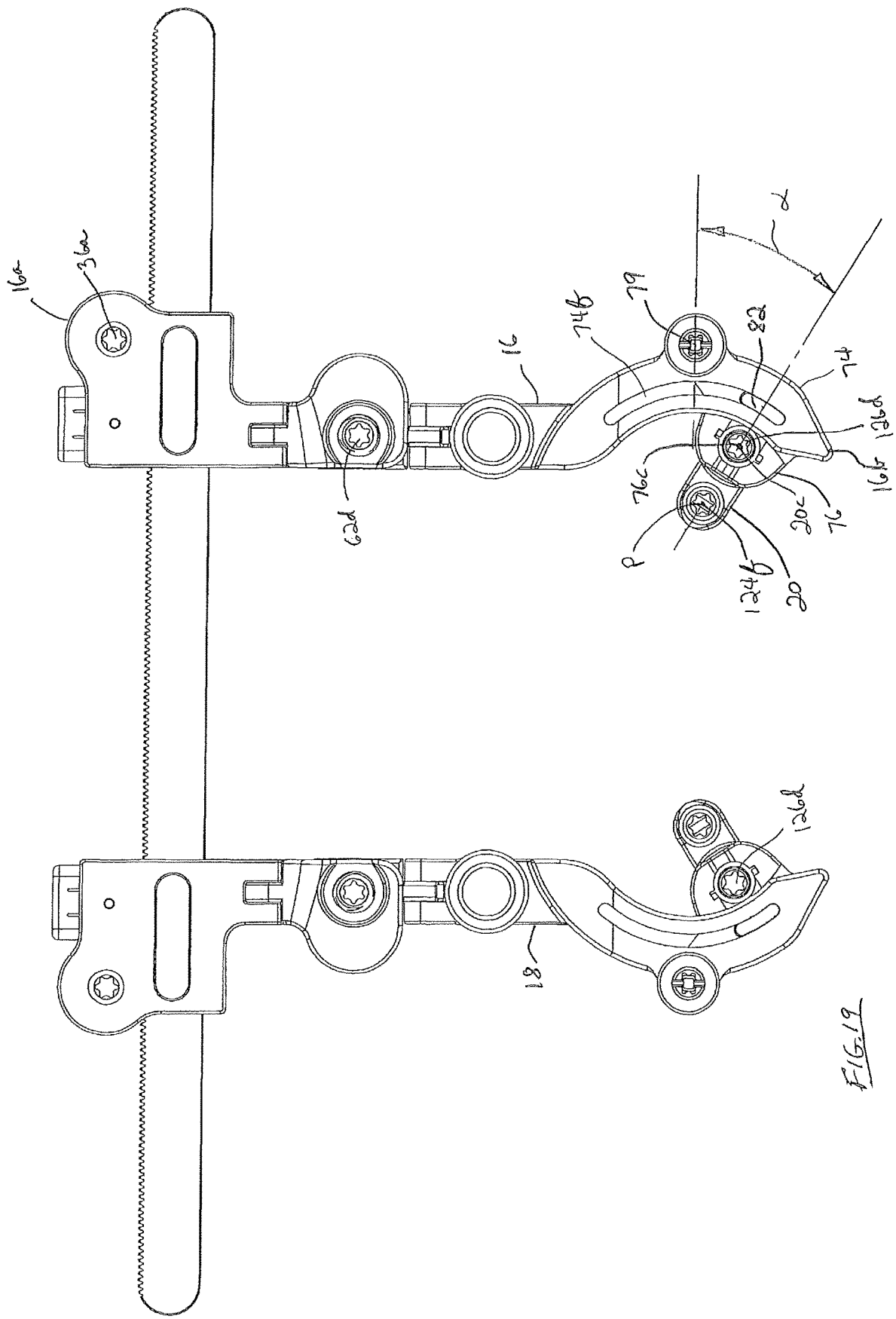

FIG. 19 is a top plan view of the retractor view of FIG. 1 with retractor blades attached thereto illustrating the articulation of the blades to their distalmost angular position.

Figure 20:
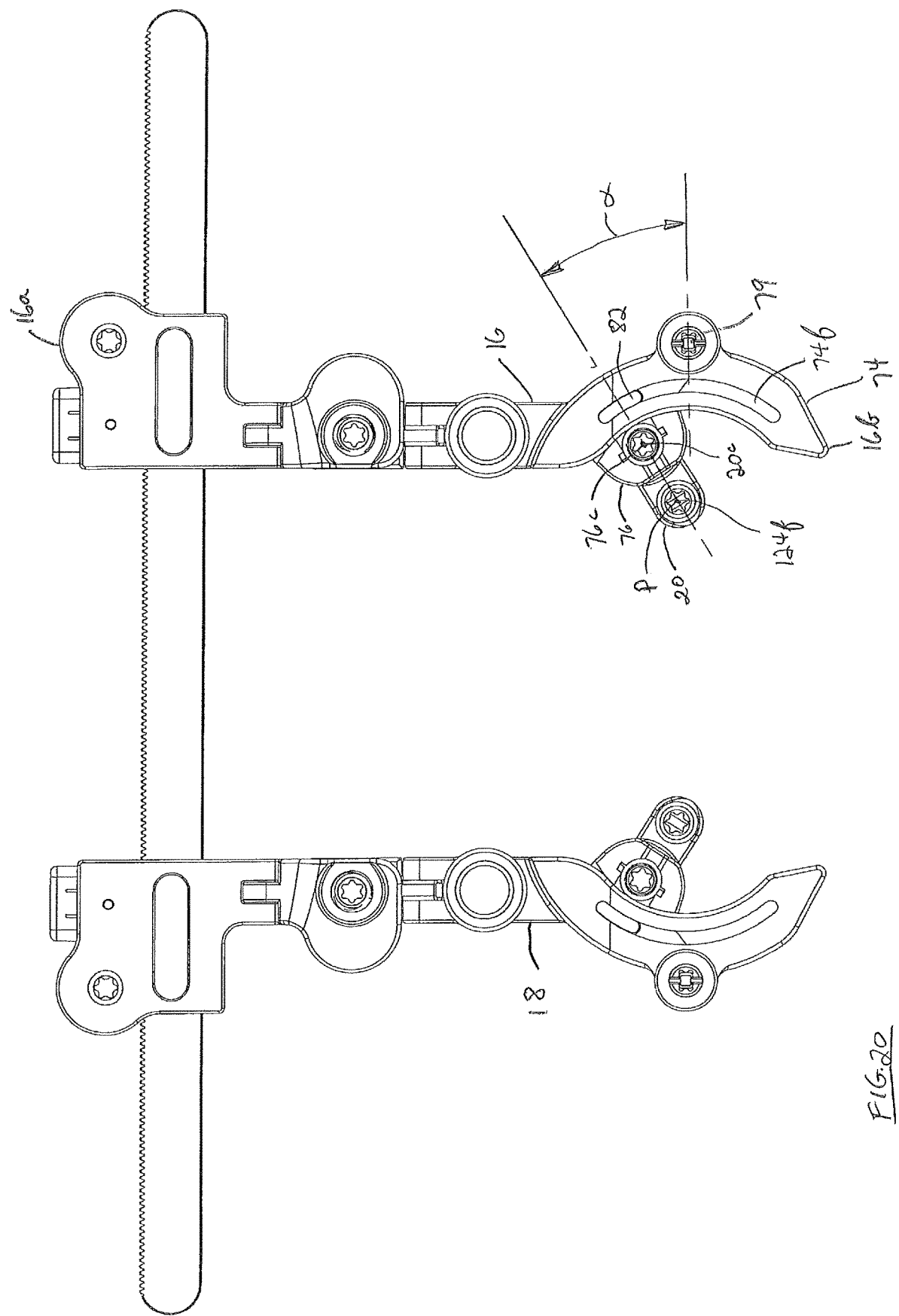

FIG. 20 is a top plan view of the retractor view of FIG. 1 with retractor blades attached thereto illustrating the articulation of the blades to their proximal most angular position.

Figure 21:
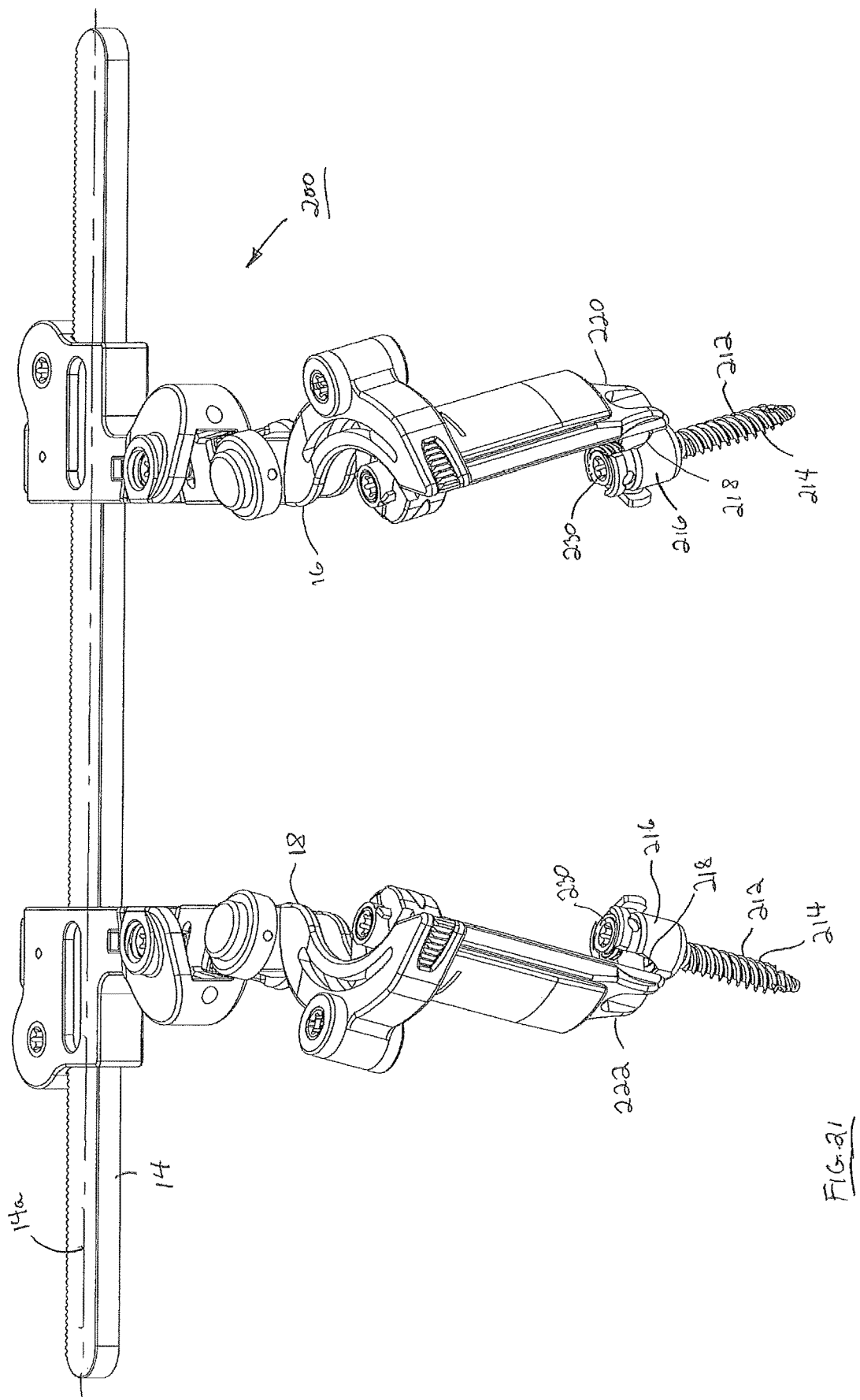

FIG. 21 is a top perspective of a screw-based retractor for use during spinal surgery in accordance with a further embodiment of the present invention.

Figure 22:
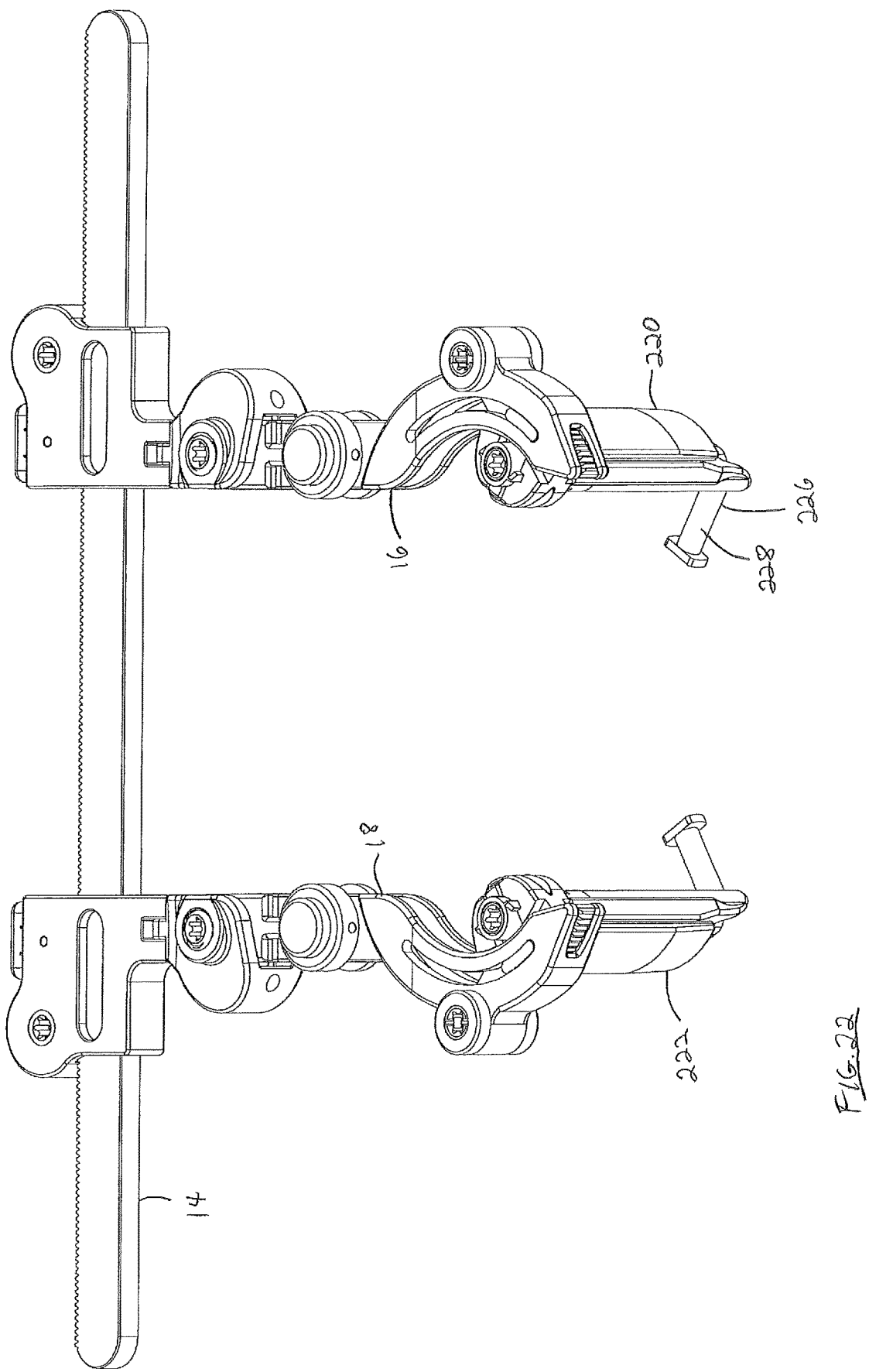

FIG. 22 is a top perspective view of the retractor of FIG. 21 prior to attachment to pedicle screws.

Figure 23:
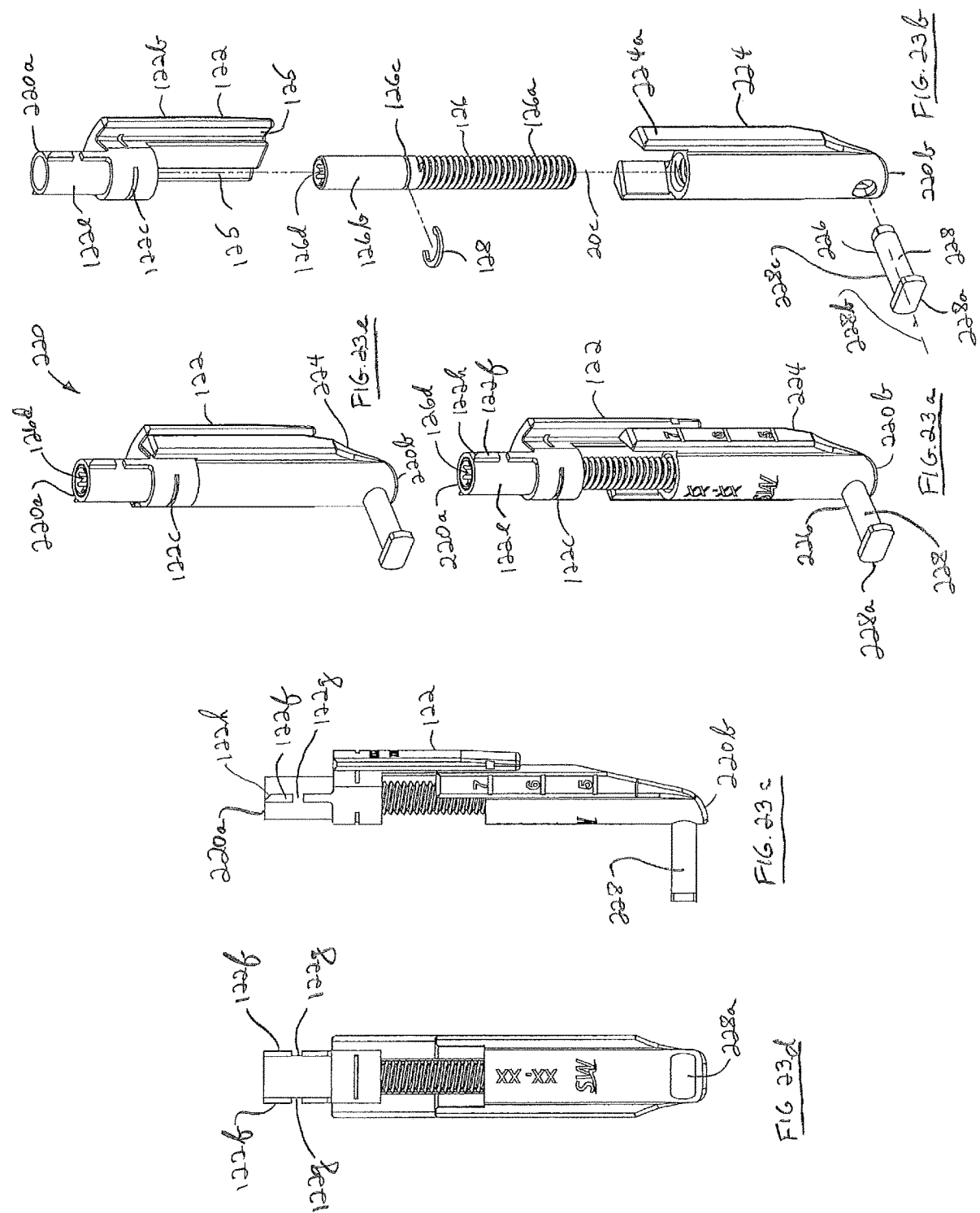

FIG. 23a is a top perspective view of a retractor blade of the retractor embodiment shown in FIG. 22, with the blade being in a fully expanded condition.

FIG. 23b is a top perspective exploded view of the retractor blade of FIG. 23a.

FIG. 23c is a side elevation view of the retractor blade of FIG. 23a.

FIG. 23d is a front elevation view of the retractor blade of FIG. 23a.

FIG. 23e is a top perspective view of the retractor blade of the retractor embodiment shown in FIG. 22, with the retractor blade being in a fully contracted condition.

Figure 24:
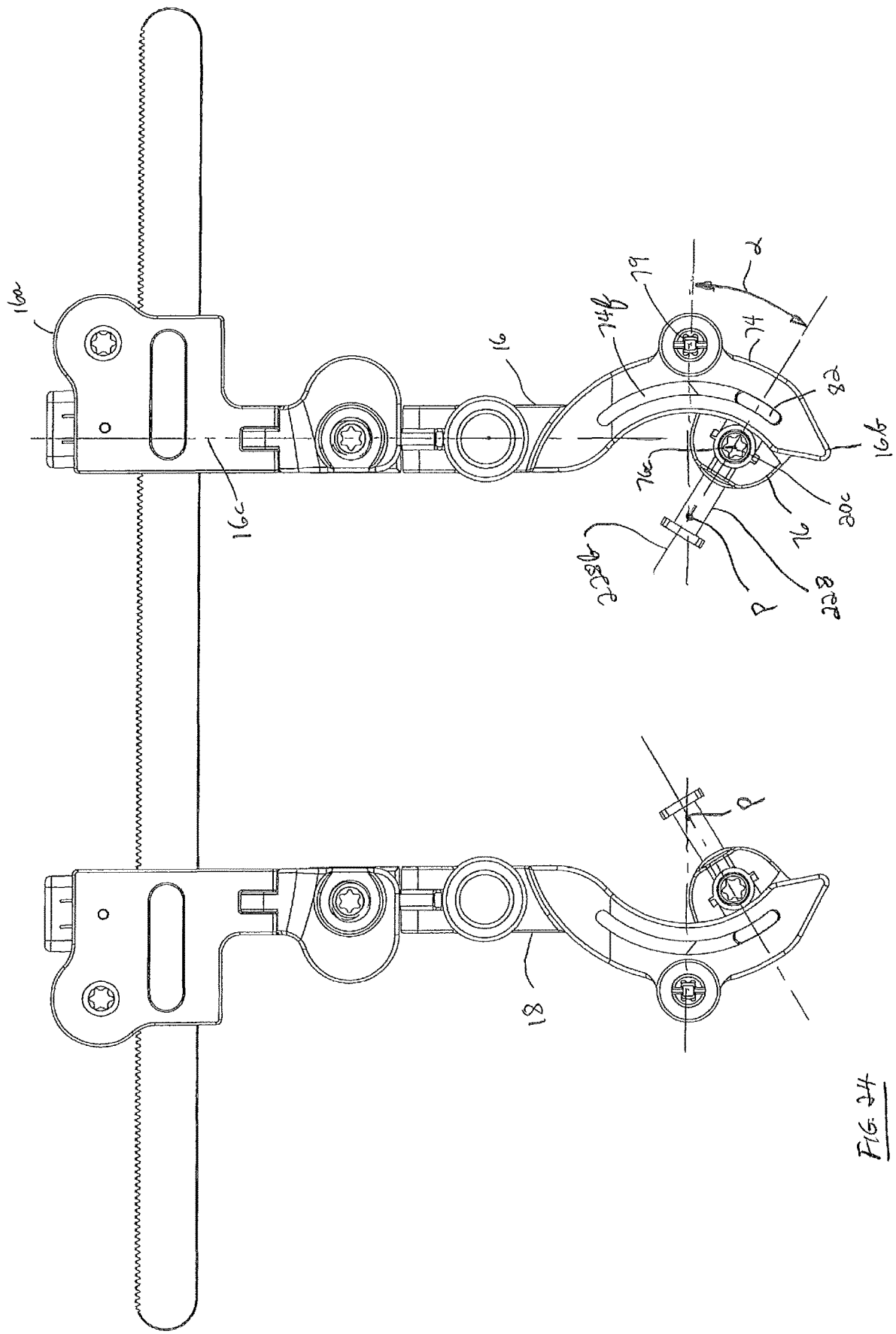

FIG. 24 is a top plan view of the retractor view of FIG. 22 illustrating the articulation of the retractor blades to their distalmost angular position.

Figure 25:
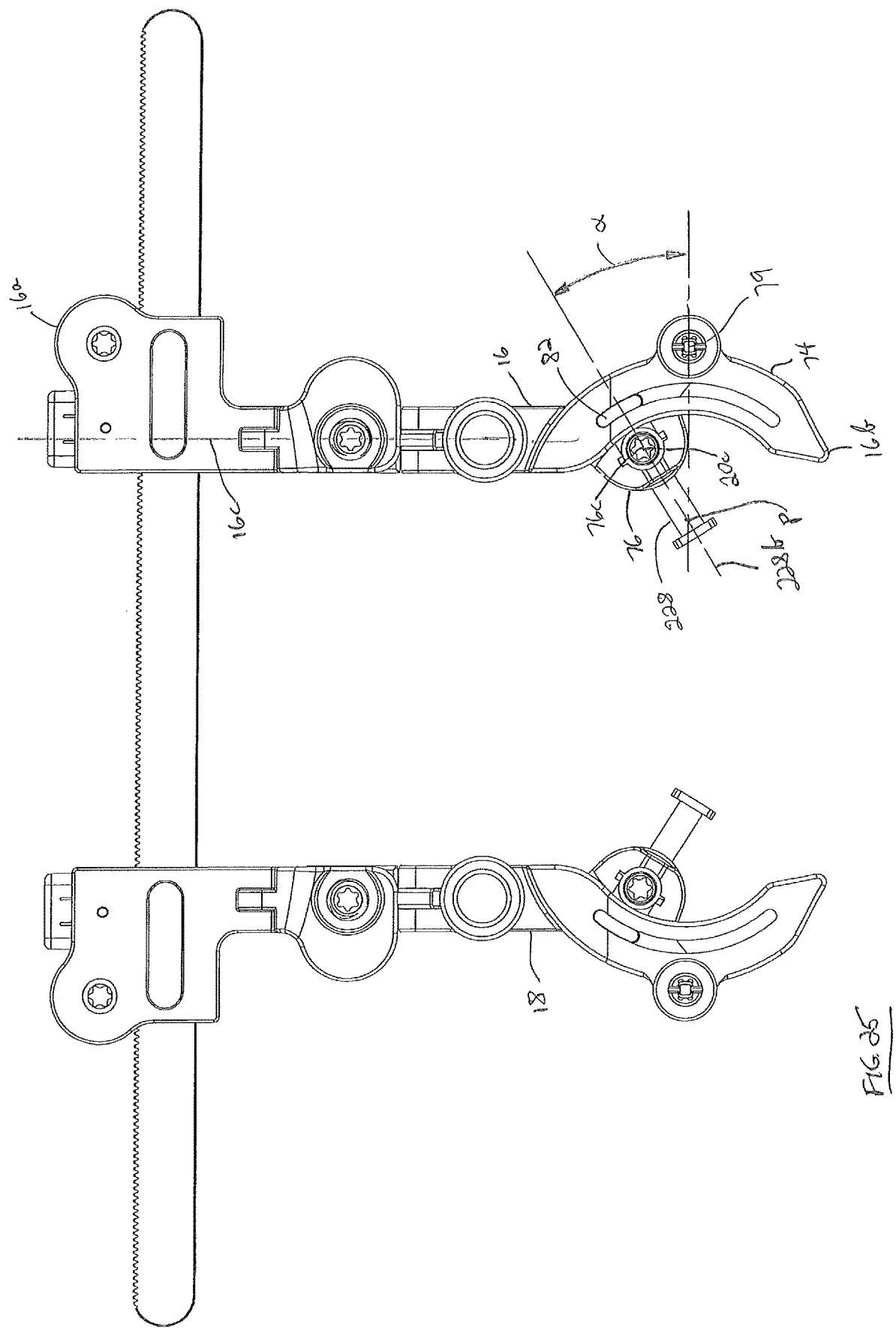

FIG. 25 is a top plan view of the retractor view of FIG. 22 illustrating the articulation of the retractor blades to their proximal most angular position.

Figure 26:
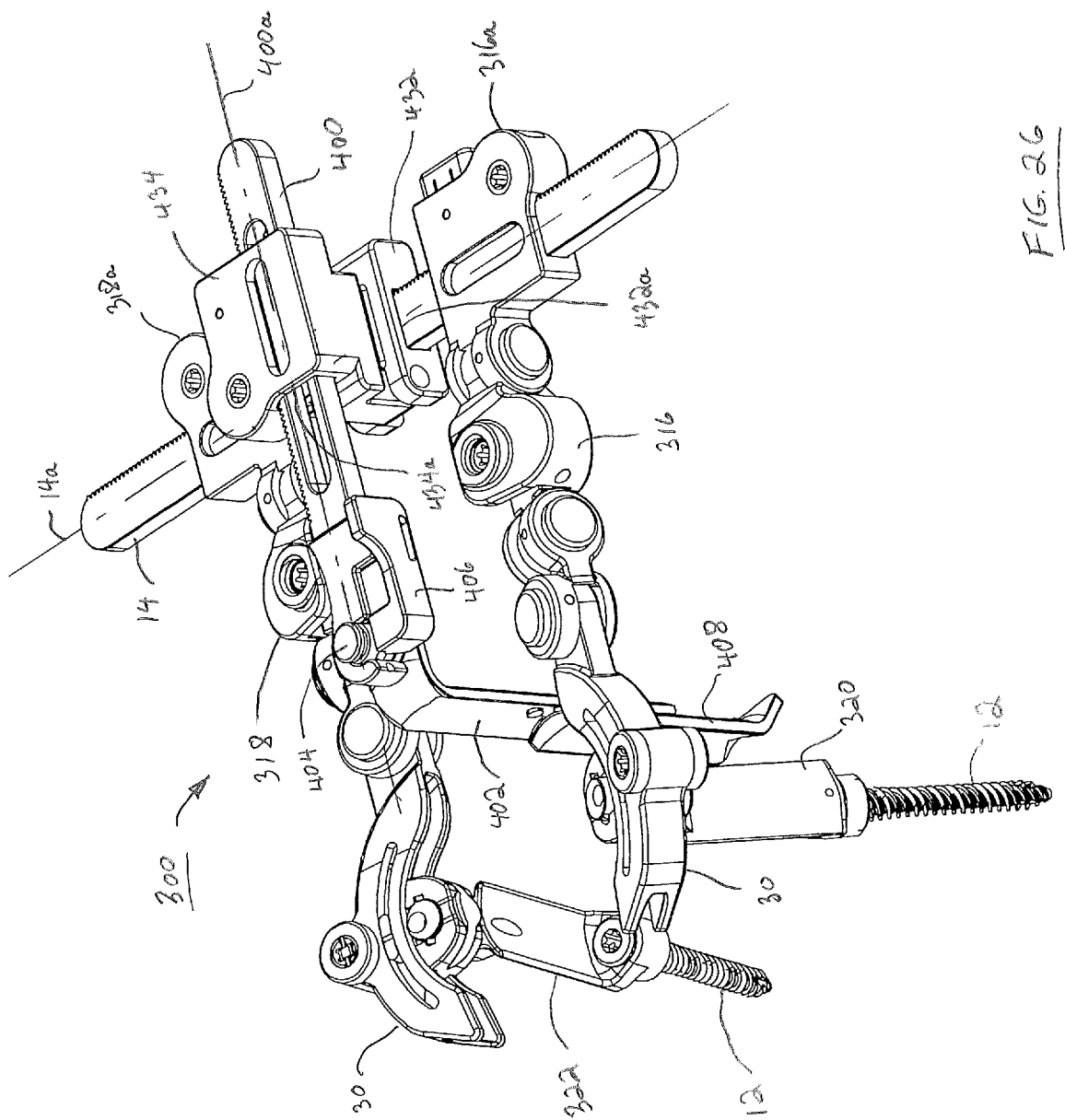

FIG. 26 is a top perspective of a screw-based retractor for use during spinal surgery in accordance with another embodiment of the present invention.

Figure 27:
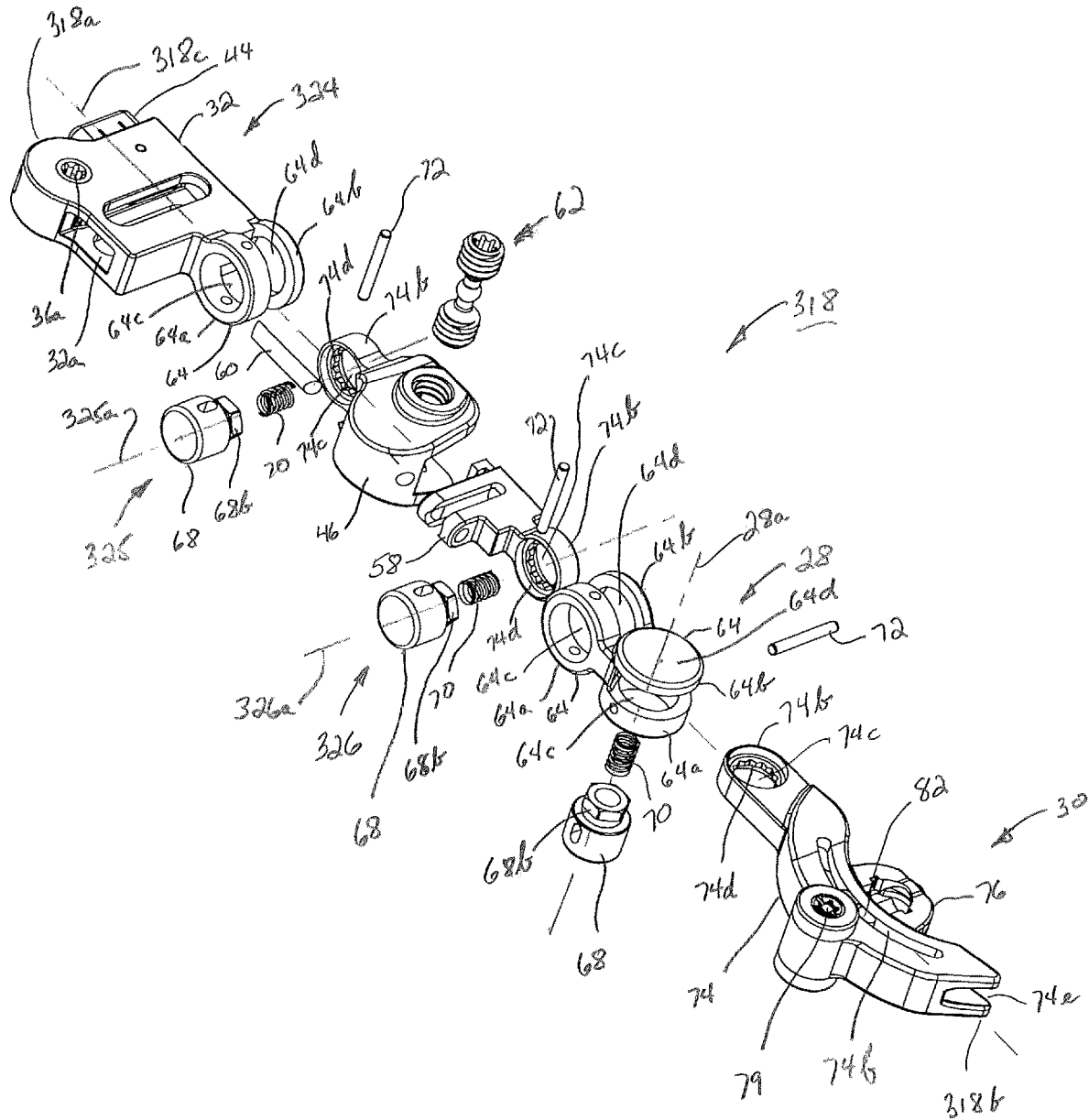

FIG. 27 is a top perspective exploded view of a retractor arm of the retractor of FIG. 26.

FIG. 28 is a side elevation view of a fixed length retractor blade of the retractor embodiment shown in FIG. 26.

FIG. 28a is a cross-sectional view of the retractor blade screw attachment as seen along viewing lines XXVIII-XXVIII of FIG. 28

FIG. 29 is a top perspective view of the fixed length retractor blade shown in FIG. 28.

Figure 30:
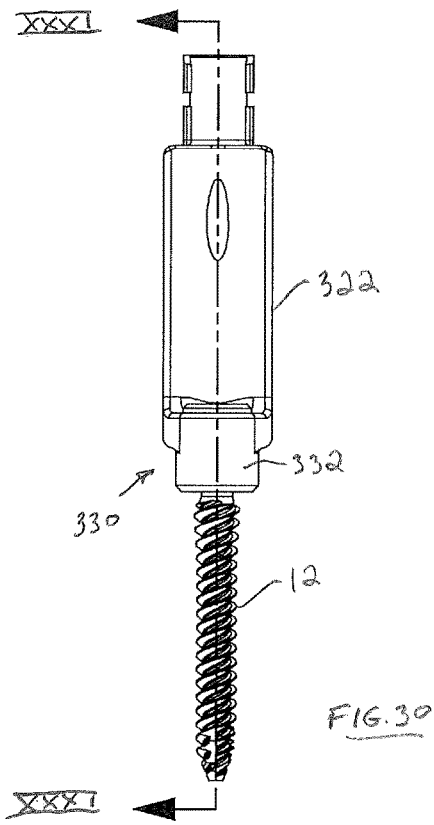

FIG. 30 is a front elevation view illustrating the connection between the retractor blade of FIG. 28 and a bone screw.

Figure 31:
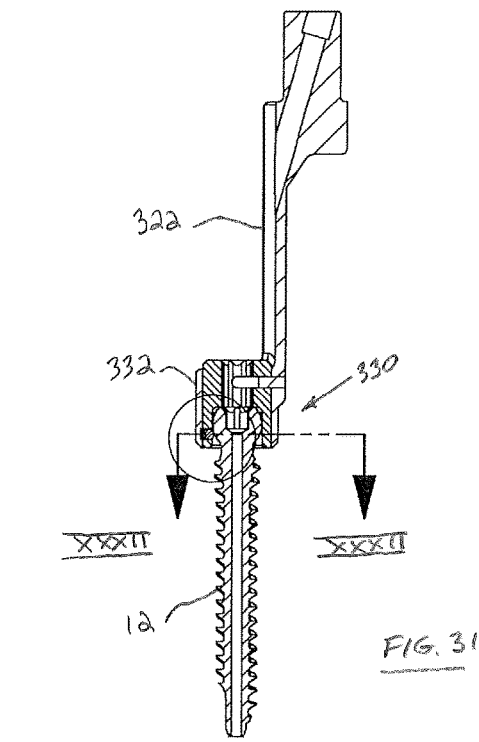

FIG. 31 is a cross-sectional view of the retractor blade and bone screw as seen along viewing lines XXXI-XXXI of FIG. 30.

Figure 32B:
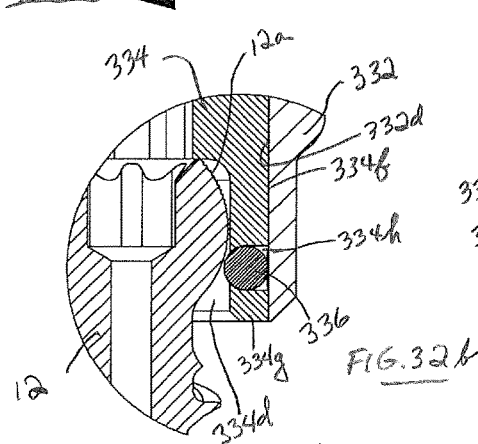
Figure 32A:
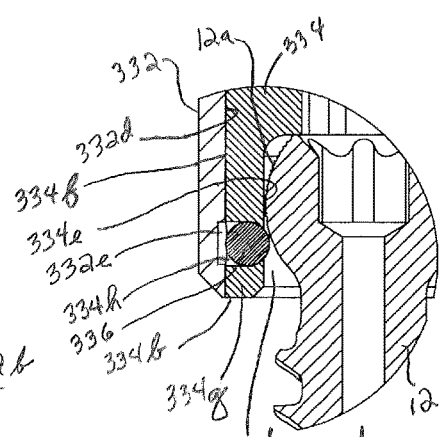

FIG. 32a is an enlarged view of the circled portion of FIG. 31, wherein the retainer rotatably supported in outer locking sleeve of the retractor blade is in a first position allowing ingress of the head of the bone screw.

FIG. 32b is an enlarged view of the circled portion of FIG. 31, wherein the retainer rotatably supported in outer locking sleeve of the retractor blade is in a second position preventing egress of the head of the bone screw.

Figure 33B:
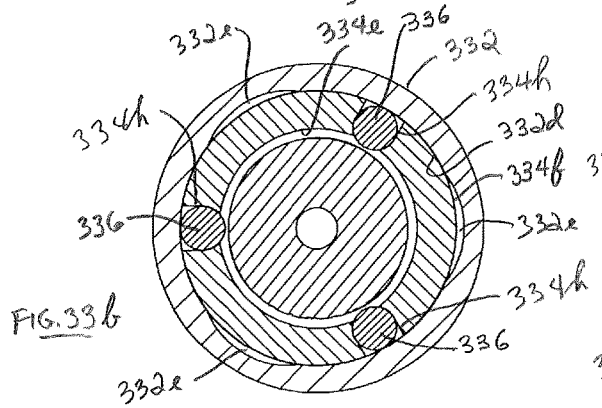
Figure 33A:
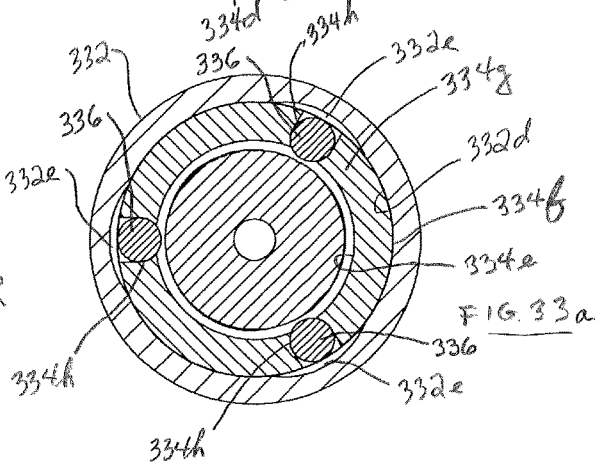

FIG. 33a is a cross-sectional view of the retractor blade and bone screw as seen along viewing lines XXXII-XXXII of FIG. 31, wherein the retainer rotatably supported in outer locking sleeve of the retractor blade is in the first position of FIG. 32a.

FIG. 33b is a cross-sectional view of the retractor blade and bone screw as seen along viewing lines XXXII-XXXII of FIG. 31, wherein the retainer rotatably supported in outer locking sleeve of the retractor blade is in the second position of FIG. 32b.

FIG. 34 is a top perspective of a screw-based retractor for use during spinal surgery in accordance with yet a further embodiment of the present invention.

FIG. 35 is a top perspective view of a fixed length retractor blade of the retractor embodiment shown in FIG. 34.

FIG. 36 is a top perspective exploded view of the fixed length retractor blade of FIG. 35.

DESCRIPTION OF THE EMBODIMENTS

For the purposes of promoting and understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Traditional polyaxial pedicle screws comprise an elongate shaft threaded at one end and a head, typically having a spherical surface, at the other end. A yoke having a U-shaped slot for receiving a fixation rod is typically pre-assembled to the screw head in a manner to allow articulating movement of the yoke relative to the threaded shaft. In a modular pedicle screw construction, the yoke is configured to be articulatingly attached to the screw head subsequent to the threaded installation of the threaded shaft into a pedicle. The screw-based retractor of the subject invention is applicable for use with both a traditional polyaxial pedicle screw after threaded installation into a pedicle or with a modular polyaxial pedicle screw prior to attachment of the yoke to the pedicle screw head. In the particular arrangement shown in FIG. 1, a screw-based retractor 10 is configured to make polyaxial connection to a head of modular pedicle screw 12 that is attached to a pedicle of a spine of a patient., as will be described. Retractor 10 is configured to distract and compress vertebral bodies and retract soft tissue during spinal surgery providing up to at least seven degrees of freedom to facilitate the surgical approach and to accommodate patient anatomy.

Retractor 10 comprises an elongate rack 14 having a longitudinal rack axis 14a, a pair of spaced arms 16 and 18, each of which are slidably translatable along rack 14, each arm 16, 18 comprising a respective blade 20 and 22 releasably attached thereto. The components of each retractor arm 16 and 18 are substantially identical and, as such, only the details of the components of retractor arm 16 will be described except as noted, it being understood that such description applies equally to the components of retractor arm 18.

Figure 2:
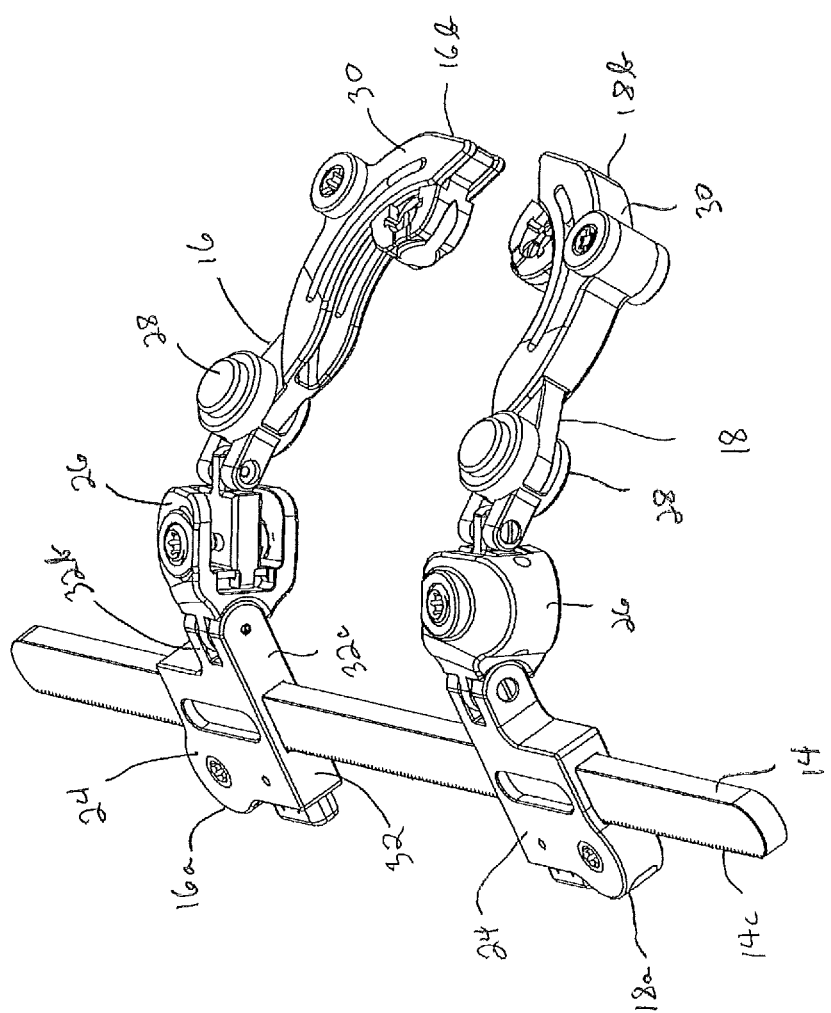
FIG. 2 is a top perspective view of the retractor of FIG. 1 prior to releasable attachment of the modular expandable blades.
Figure 3:
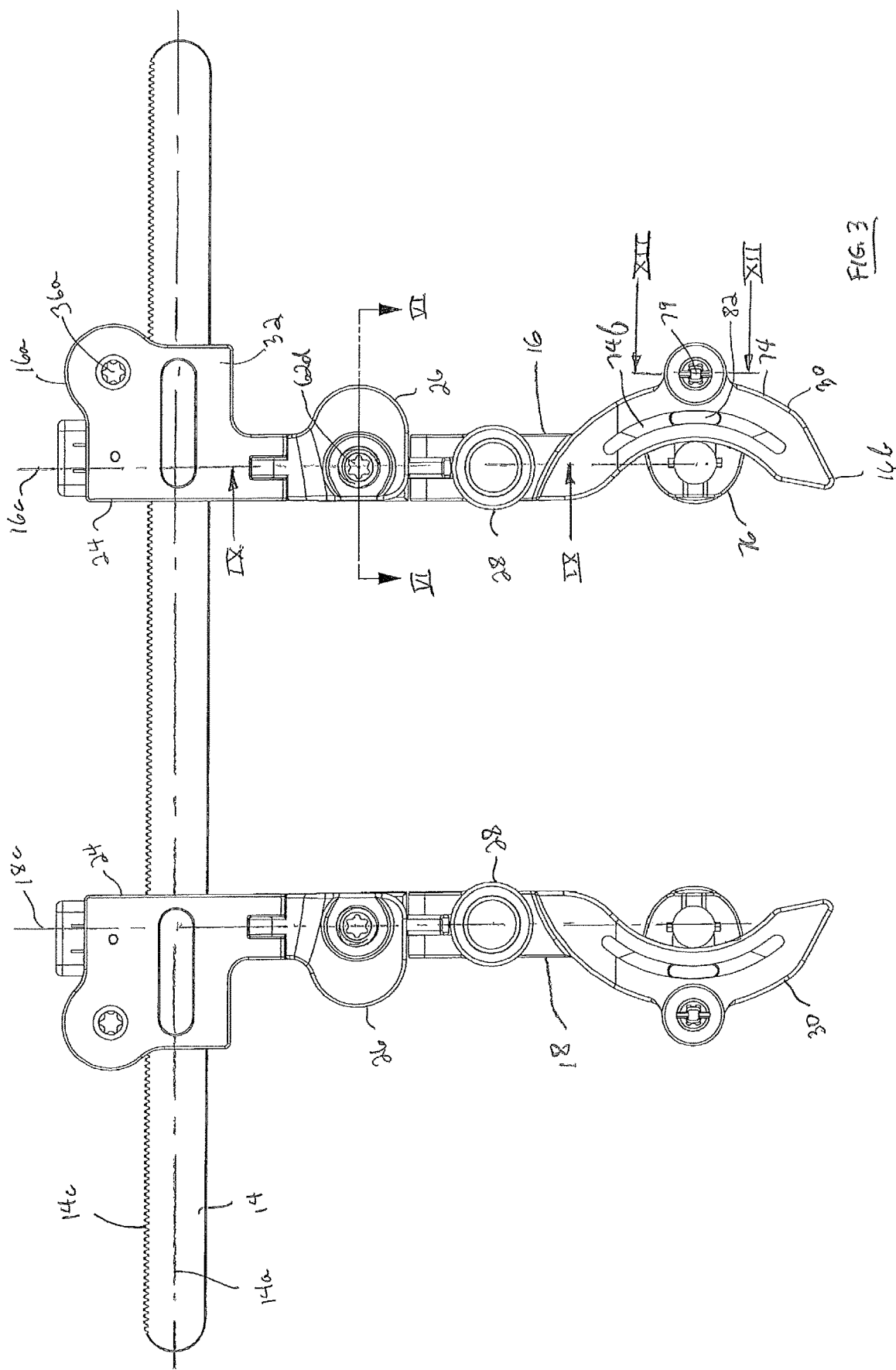
FIG. 3 is a top plan view of the retractor view of FIG. 2.

Turning now to FIGS. 2 and 3, retractor 10 is shown prior to the releasable attachment of blades 20 and 22. Each said arm 16, 18 is multi-faceted and defines a respective arm axis 16c, 18c extending generally transversely relative to rack axis 14a. Rack 14, which is preferably metal, such as stainless steel, comprises gear teeth 14c formed along one lateral edge of rack 14, substantially over the entire length of rack 14. Teeth 14c facilitate the movement and locking of arms 16 and 18 toward and away from each other along rack 14. Each arm 16 and 18 has a respective proximal end 16a and 18a and a distal end 16b and 18b. Proximal ends 16a and 18a slidably attach to rack 14 and distal ends 16b and 18b are releasably attachable to respective blades 20 and 22. Each arm 16 and 18 comprises a retraction control unit 24, a pivot control link 26, a swivel joint link 28 and a blade arm assembly 30, such components being substantially identical for each arm 16 and 18. Retraction control unit 24 defines a proximal portion slidably attached to rack 14 at the respective proximal ends 16a, 18a of each arm 16, 18 while blade arm assembly 30 defines a distal portion releasably attachable at the respective distal ends 16b, 18b of each arm 16, 18 to blades 20, 22.

Further details of the retractor arm components are described with reference to FIGS. 4-5. Retraction control unit 24 comprises a housing 32 having an opening 32a extending therethrough for slidable receipt of rack 14. On the proximal side of opening 32a, housing 32 includes therewithin a retraction gear 34 coupled for rotation with a gear shaft 36. Retraction gear 34 comprises about its circumference a plurality of gear teeth 34a that intermesh with gear teeth 14c of rack 14. Gear shaft 36 comprises a drive socket 36a exposed exteriorly of housing 32 at the top and a similar drive socket 36a at the bottom (not shown). Each drive socket 36a is configured as a Torx socket or other suitable configuration for engagement with a driving instrument to rotate gear shaft 36 and hence retraction gear 34. Also included within housing 32 on the proximal side of opening 32a is a spring-loaded pawl 38 pivotably supported about a pivot pin 40. One end 38a of pawl 38 comprises a relatively sharp edge for engagement with rack gear teeth 14c while an opposite end 38b is contacted by a spring 42. Spring 42 biases end 38b of pawl 38 proximally causing opposite edge 38a to be urged normally distally in engagement with rack gear teeth 14c. Pawl end 38a is configured such that housing 32, and hence arm 16, is movable away from but not towards arm 18 upon rotation of retraction gear 34. A movable retraction control button 44 is supported by housing 32 for engagement with pawl end 38b. Distal movement of button 44 causes pawl end 38b to pivot about pin 40 distally against the bias of spring 42, separating pawl edge 38a from rack teeth 14c and allowing free transverse movement of retraction control unit 24 both toward and away from arm 18. Such transverse sliding movement of housing 32 along rack 14 in both directions establishes a first degree of freedom of movement of a blade 20 attached to the distal end 16b of arm 16 relative to rack 14.

Housing 32 on the distal side of opening 32a comprises a pair of laterally spaced hinge arms 32b and 32c. Hinge arms 32b and 32c extend distally from housing 32 and substantially parallel to arm axis 16c. Hinge arms 32b and 32c define a recess 32d therebetween for hinged receipt of a portion of pivot control link 26, as will be described.

Figure 4:
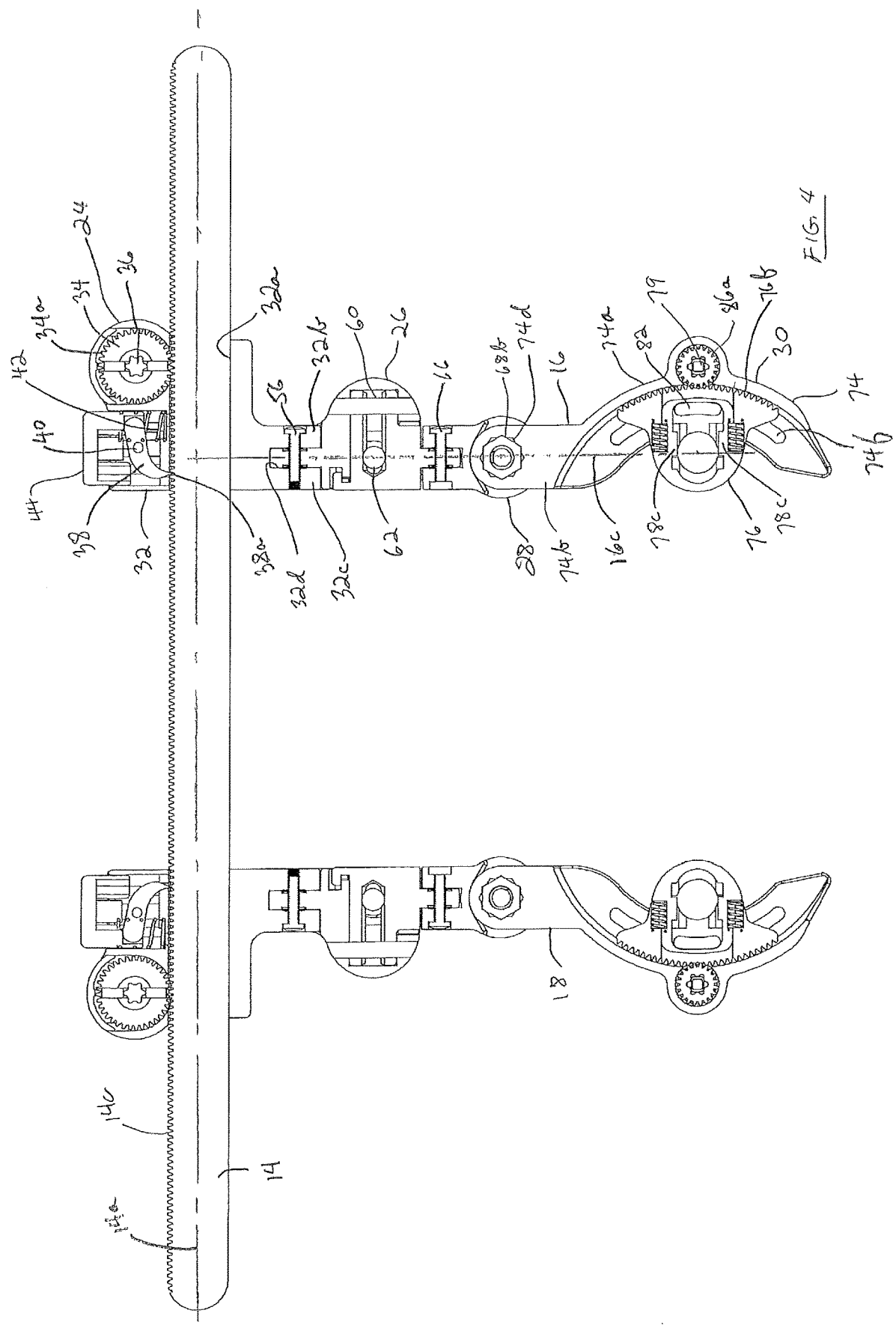
FIG. 4 is a longitudinal cross-sectional view of the retractor view of FIG. 3.
Figure 5:
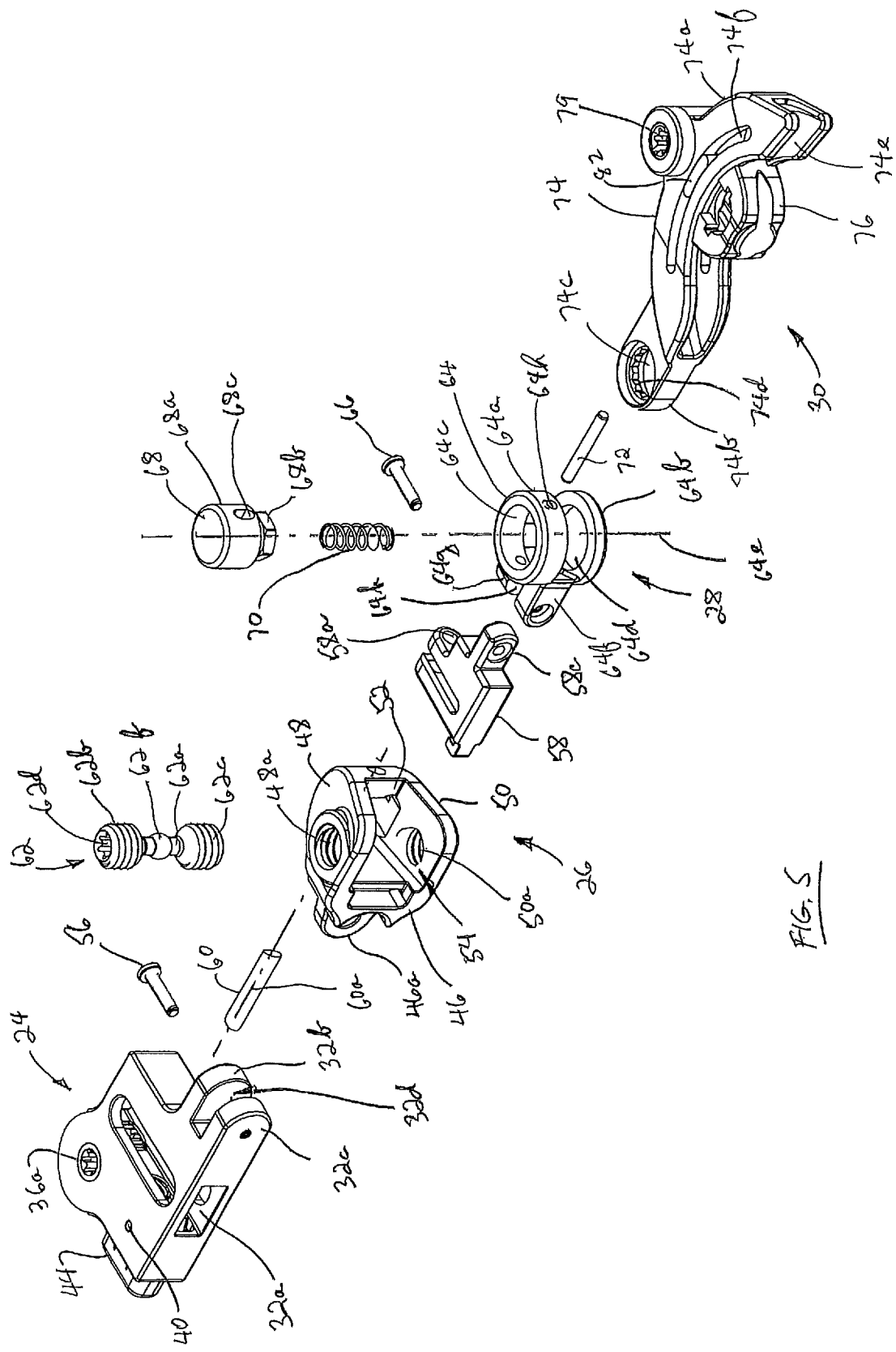
FIG. 5 is a top perspective exploded view of a retractor arm of the retractor of FIG. 1.
Figure 6:
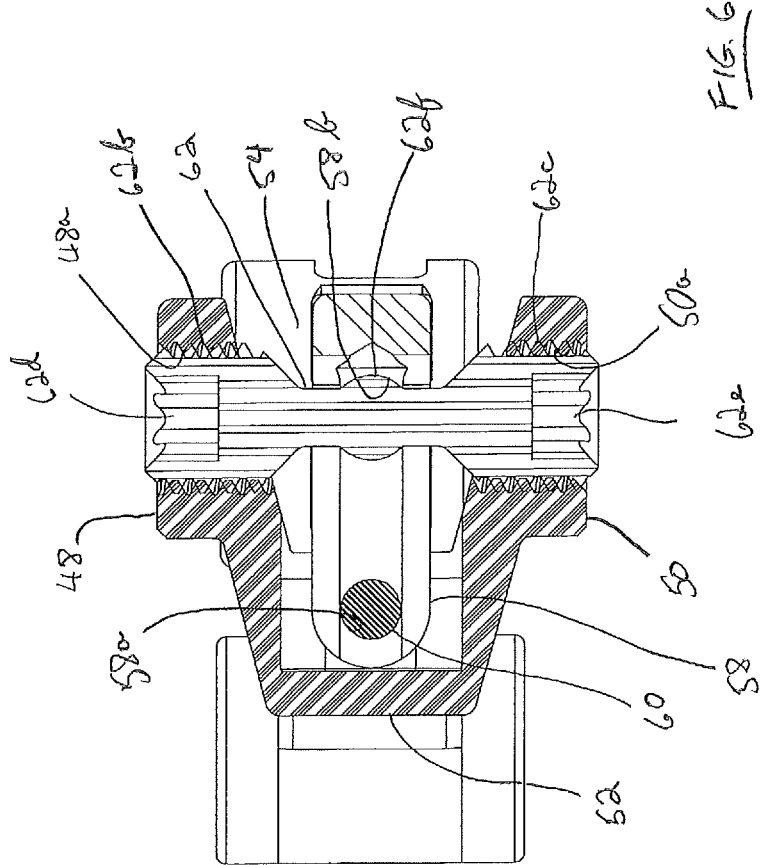
FIG. 6 is a cross-sectional view of the retractor arm as seen along viewing line VI-VI of FIG. 3.

With reference yet to FIGS. 4-5, and now to FIG. 6, details of pivot control link 26 are described. Pivot control link 26 comprises a link member 46 includes an upper plate 48 and a lower plate 50 joined by a side wall 52. Upper plate 48, lower plate 50 and side wall 52 define an open compartment 54. A hinge arm 46a projects proximally from link member 46 and extends into recess 32d of housing 32 of retraction control unit 24. Hinge arms 32c and 32d of retraction control unit 24 are hinged with hinge arm 46a of link member 46 by an elongate pin 56, which may be in the form of a screw. Pin 56 lies substantially parallel to rack axis 14a and allows pivot control link 26 and a blade 20 attached to the distal end 16b of arm 16 to move in a second degree of freedom relative to rack 14.

Pivot control link 26 includes a short link 58 supported within compartment 54 for pivotal movement by a pivot pin 60 having an axis 60a extending though an opening 58a of short link 58. Axis 60a of pivot pin 60 is substantially parallel to but offset from arm axis 16a. A pivot stud 62 is supported by link member 46 to effect pivotal movement of short link 58 relative to link member 46. Pivot stud 62 is generally elongate having a central shaft 62a and opposing upper and lower threaded ends 62b and 62c. Both ends 62b and 62c comprise a respective drive socket 62d and 62e exposed exteriorly of link member 46. Drive sockets 62d and 62e are each configured as a Torx socket or other suitable configuration for engagement with a driving instrument to rotate pivot stud and pivot short link 58, as will be described. Upper threaded end 62b is threadably received in a threaded opening 48a extending through upper plate 48 while lower threaded end 62c is threadably received in a threaded opening 50a extending through lower plate 50. Central shaft 62a of pivot stud 62 comprises a bulbous portion 62f that is captured within a pocket 58b that is slightly larger than bulbous portion 62f and is formed interiorly of short link 58. As such, upon rotation of pivot stud 62 by a suitable instrument engaged to either the upper or lower drive sockets 62d or 62e, pivot stud 62 will move upwardly or downwardly relative to link member 46. Such movement of pivot stud 62 will cause short link 58 to pivot about pin axis 60a by virtue of the bulbous portion 62f being captured in link pocket 58b. Accordingly, such pivoting or toeing movement of short link 58 will cause swivel joint link 28 and blade arm assembly 30 with a blade 20 attached thereto to pivot about pin axis 60a establishing a third degree of freedom of movement of blade 20. Short link 58 comprises a hinge arm 58c projecting distally from short link 58 and substantially parallel to arm axis 16c for hinged receipt with a portion of swivel joint link 28, as will be described. It should be appreciated that pivot control link 26 is reversible in the sense that it may be inverted and used in arm 18, whereby drive socket 62e would be facing upwardly so as to provide the ability to actuate the toeing feature from above during surgery.

Figure 7:
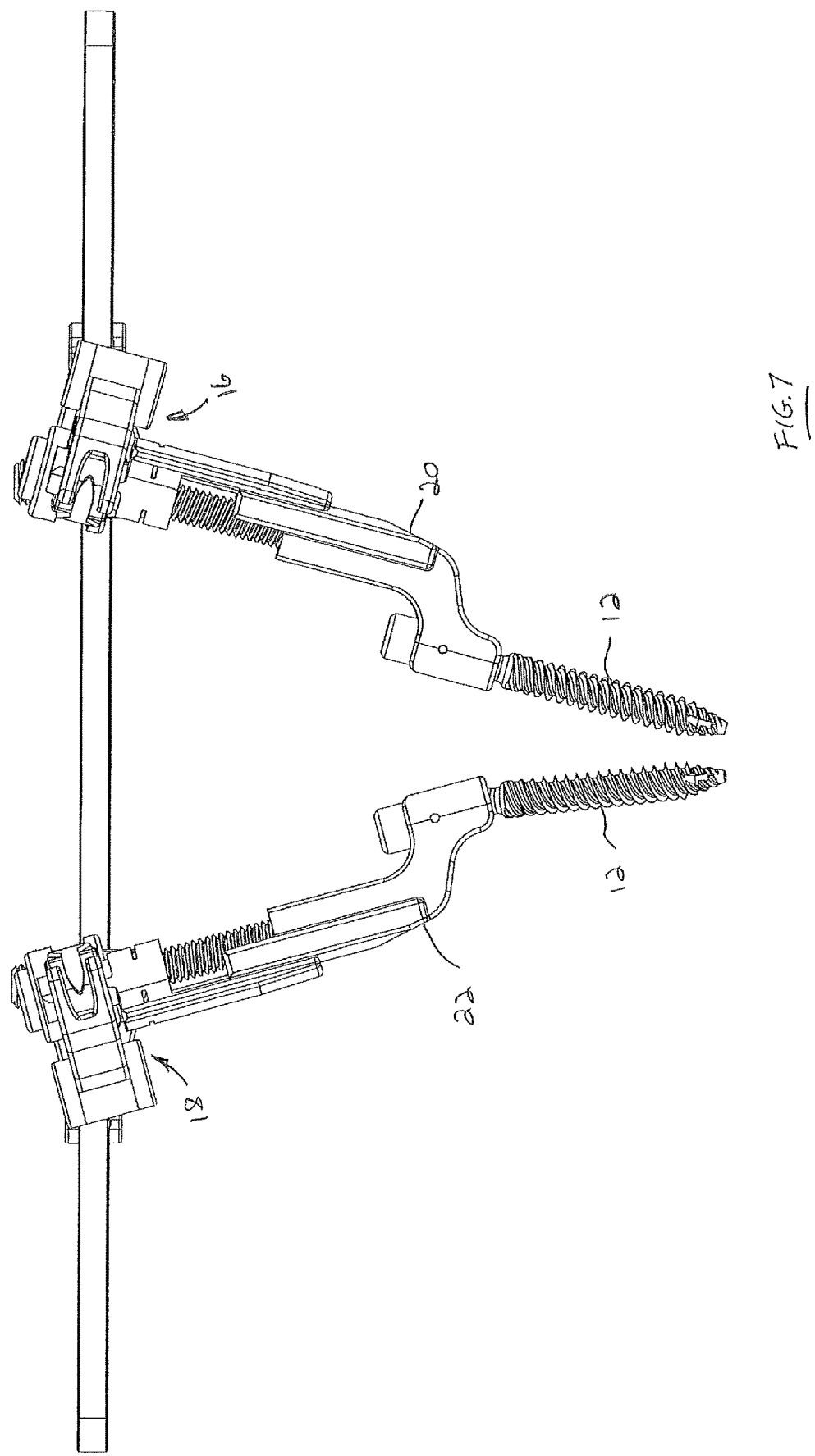
FIG. 7 is a side elevation view of the retractor of FIG. 1 with each of the blades in a toed position directed toward each other.
Figure 8:
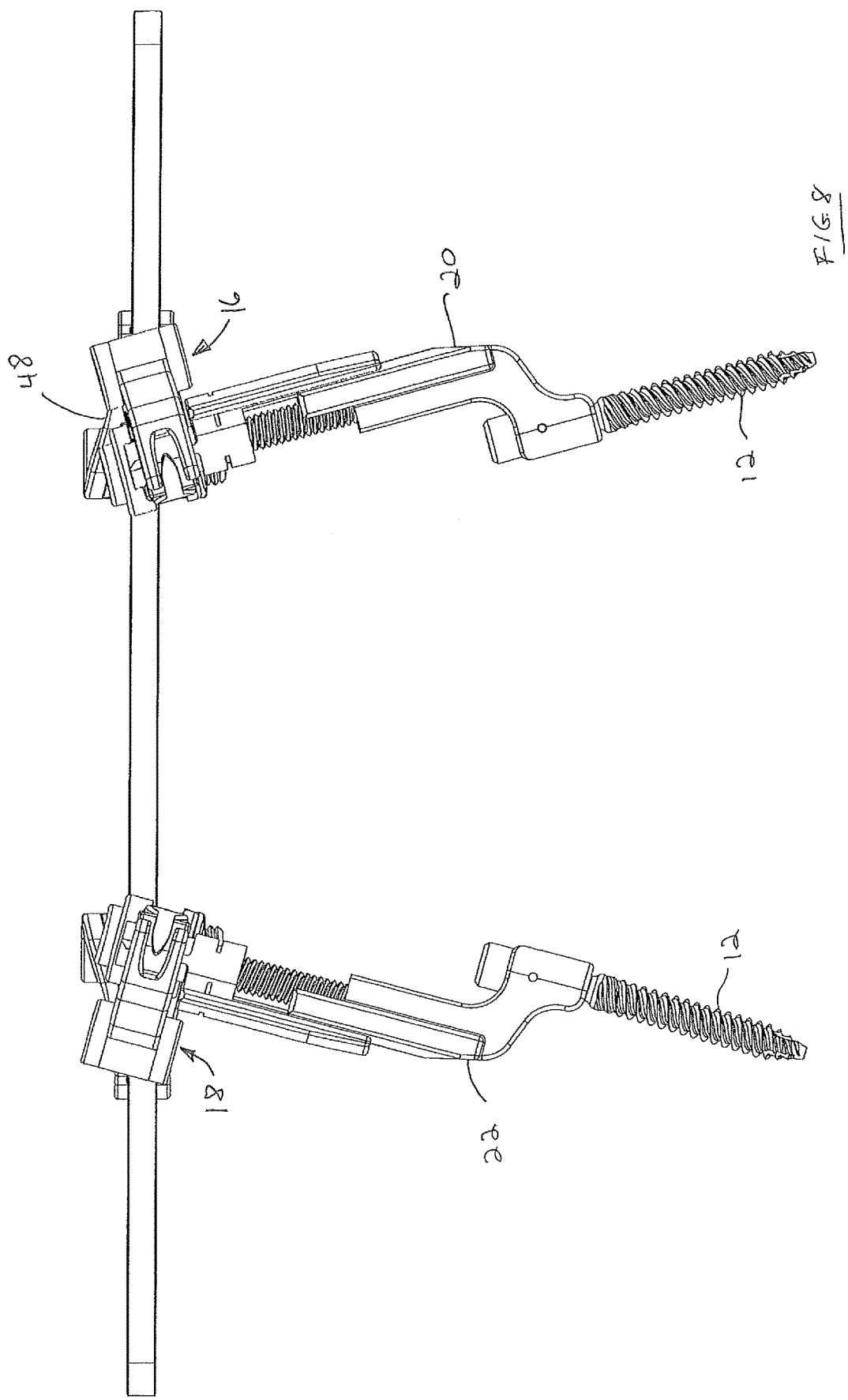
FIG. 8 is a side elevation view of the retractor of FIG. 1 with each of the blades in a toed position directed away from each other.

FIG. 7 shows screw-based retractor 10 in the embodiment of FIG. 1 wherein each of the blades 20 and 22 are toed inwardly toward each other in accordance with the concepts described herein while FIG. 8 shows such screw-based retractor 10 with blades 20 and 22 toed outwardly away from each other. It should be appreciated, however, that one blade may be toed toward the other while the other blade may be toed away.

Figure 9:
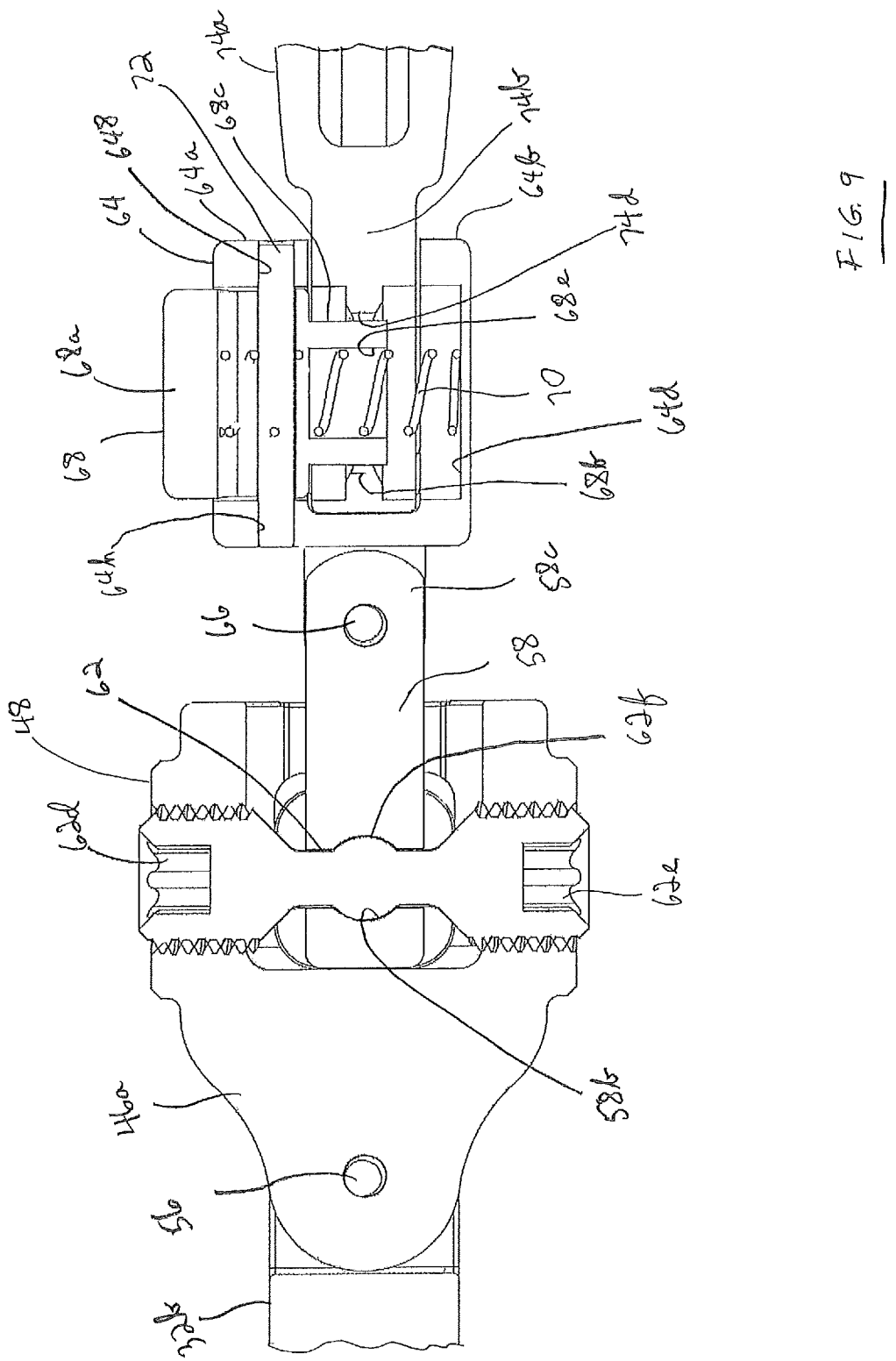
FIG. 9 is a cross-sectional view of the retractor arm as seen along viewing line IX-IX of FIG. 3.
Figure 10A:
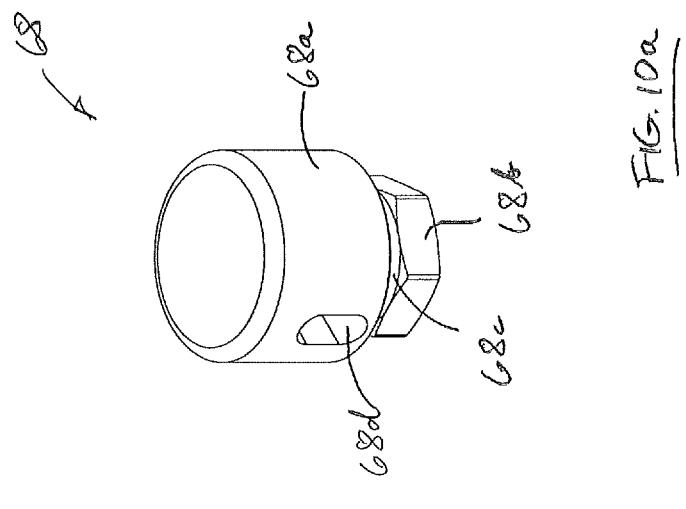
FIG. 10a is a top perspective view of the hex button of the swivel joint link of the retractor arm.
Figure 10B:
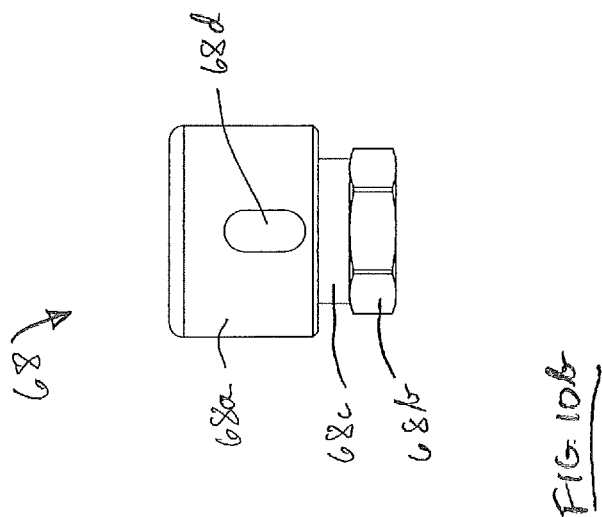

With further reference to FIGS. 4-5 and now to FIGS. 9 and 10, details of swivel joint link 28 are described. Swivel joint link 28 comprises a generally cylindrical body 64 including an upper ring 64a and a lower ring 64b spaced therefrom. Upper ring 64a has a generally circular opening 64c extending therethrough and lower ring 64b has a generally circular recessed floor 64d, opening 64c defining a swivel axis 64e. Swivel body 64 includes a pair of laterally spaced hinge arms 64f and 64g extending proximally therefrom and substantially parallel to arm axis 16c. Hinge arms 64f and 64g define a recess 64h therebetween for hinged receipt of hinge arm 58c of pivot control link 26. Hinge arms 64f and 64g of swivel joint link 28 are hinged with hinge arm 58c of short link 58 by an elongate pin 66. Pin 66 lies substantially parallel to rack axis 14a and allows swivel joint link 28 and a blade 20 attached to the distal end 16b of arm 16 to move in a fourth degree of freedom relative to rack 14. Upper ring 64a has diametrically spaced openings 64h formed therethrough, as will be described.

A manually depressible hex button 68 as depicted in FIG. 10 is movably supported by body 64 of swivel joint link 28. Hex button 68 includes a generally cylindrical upper portion 68a and a shaped lower portion 68b, preferably having a hex configuration, although other polygonal shapes may be used. Upper portion 68a is sized and configured to fit and slide within opening 64c along swivel axis 64e. Between upper portion 68a and lower portion 68b, button 68 includes an intermediate portion 68c. Intermediate portion 68c has a reduced maximum dimension, generally smooth and cylindrical, relative to upper portion 68a and lower portion 68b, the purpose and function of which will be described. An elongated slot 68d extending along swivel axis 64e is formed through upper portion 68a. One end of a compression spring 70 is supported on swivel body floor 64d and the opposite end is received within a cavity 68e formed interiorly of button 68, as illustrated in FIG. 9. A pin 72 extends through swivel body openings 68h and through slot 68d to assemble hex button 68 and swivel body 64 together. In assembly, elongate slot 68d and pin 72 limit travel of button 68 along swivel axis 64e. In the normal condition spring 70 biases hex button 68 in the upward position to lock swivel joint link 28 with blade arm assembly 30, while in the depressed downward position rotation of the blade arm assembly 30 relative to swivel joint link 28 is permitted, as will be described.

Turning now to FIGS. 11a and 11b with further reference still to FIGS. 4, 5 and 9, details of the blade arm assembly 30 are described. Blade arm assembly 30 is identical for each retractor arm 16 and 18, and as such the blade arm assembly 30 of retractor arm 18 is illustrated in FIGS. 11a and 11b as more illustrative details are evident in these views. Blade arm assembly 30 comprises a blade arm 74, a blade receptacle 76 and an articulation drive mechanism 79. Blade arm 74 includes an arcuate portion 74a and an arm connector 74b projecting proximally therefrom for swivel connection to swivel joint link 28. Extending through arm connector 74b is an opening 74c having a shaped inner circumference 74d. In a particular arrangement, inner circumference 74d is configured to have a 12-point star feature for selective engagement with the hex configuration of hex button lower portion 68b, as seen in FIG. 4. It should be appreciated that the shaped inner circumference 74d may have other suitable configurations other than the 12-point star feature provided that the shaped configuration of inner circumference 74d and the shaped configuration of lower portion 68b of button 68 allow selective incremental interconnection therebetween.

Referring to FIG. 9, as described above, spring 72 normally biases hex button 68 in an upward first position in which the shaped hex surface 68b is in releasable engagement with the 12-point star feature of inner circumference 74d of arm connector 74b. Manual depression of hex button 68 causes button 68 to move downwardly into opening 64c of swivel body 64 thereby pushing hex surface 68b out from engagement with shaped inner circumference 74d until button intermediate portion 68c is in juxtaposition with shaped inner circumference 74d. In this second, depressed position, intermediate portion 68c is spaced and disengaged from shaped inner circumference 74d thereby allowing blade arm 74 to freely swivel about intermediate portion 68c and swivel axis 64e in a fifth degree of freedom of movement relative to rack 14. Upon rotatably positioning blade arm 74 to a desired new position, manual force on button 68 is removed, causing button 68 to return to the first position under the bias force of spring 70 in which hex surface 68b and shaped inner circumference 74d are in engagement thereby locking blade arm 74 in the new position. It should be appreciated that the interengagement between hex surface 68b and the 12-point star feature of shaped inner circumference 74d permits positioning of blade arm in 30-degree angular incremental orientations, although other engagement configurations for different angular positions may be used.

Blade receptacle 76 comprises a receptacle body 76a having an enclosed opening 76b for receipt of a portion of blade 20, as will be described. Blade receptacle opening 76a defines a blade receptacle opening axis 76c. A pair of approximately diametrically opposed channels 76d are formed through receptacle body 76a in communication with receptacle opening 76b and generally parallel to blade receptacle opening axis 76c. One edge 76e of receptacle body 76a is formed to have an arcuate extent comprising a plurality of gear teeth 76f extending therealong. The opposite side of receptacle body 76a has a slot 76g extending therein, slot 76g being generally orthogonal to blade receptacle opening axis 76c and communicating with receptacle opening 76b. A blade lock button 78 for releasably locking blade 20 to blade receptacle 76 is provided. Blade lock button 78 comprises an open frame 78a having an enclosed opening 78b, frame 78a being sized and configured to be slidably received in receptacle slot 76g. A pair of spaced opposing lock surfaces 78c project into lock button opening 78b. Frame 78a is inserted into slot 76g of receptacle body 76a for sliding movement therewithin. A pair of compression springs 80 is supported by receptacle body 76a and provides a bias force against surfaces 78d of lock button 78. In the normal biased position, locking surfaces 78c interfere with and close channels 76d of receptacle body 76a for locking blade 20 to blade receptacle 76. Locking surfaces 78c may be moved out of interference with channels 76d upon introduction of a portion of blade 20 into opening 76b of blade receptacle 76 or upon manual depression of button surface 78e toward receptacle body 76a to overcome the bias force of springs 80 to thereby allow release of blade 20 from blade receptacle 76, as will be described.

Edge 76e of blade receptacle 76 is inserted into a slot 74e (See FIG. 5) extending into and arcuately along arcuate portion 74a of blade arm 74. Arcuate portion 74a has a curved track 74f extending along a major extent of arcuate portion 74a, track 74f communicating with slot 74e. Blade receptacle 76 is attached to blade arm 74 by an arc key 82 which has an arcuate extent substantially less than arcuate slot 74f of blade arm arcuate portion 74a. Arc key 82 is introduced through arcuate slot 74f and through blade receptacle slot 76h where it is suitably affixed to blade receptacle body 76a, such as by friction fit and/or tack welding. Arc key 82 is sized and configured to slide within blade arm track 74f in manner to articulate a blade 20 when attached to blade receptacle 76, as will be described.

With reference still primarily to FIGS. 11a and 11b, further details of the articulation drive mechanism 79 are described. Blade arm portion 74a includes a container section 74g having an opening 74h extending therethrough, opening 74h defining an articulation drive axis 84. Opening 74h communicates with blade arm arcuate slot 74e. Supported within container opening 74h for rotation about drive axis 84 is an articulation control gear 86. Articulation control gear 86 is generally cylindrical and includes substantially centrally about its circumference a plurality of gear teeth 86a. Gear teeth 86a are formed to intermesh with gear teeth 76f extending along arcuate edge 76e of blade receptacle 76 (see FIG. 4). A first pair of substantially diametrically disposed slots 86b extends through articulation drive gear 86 on one side of gear teeth 86a and second pair of substantially diametrically disposed slots 86c extends through articulation drive gear 86 on the opposite side of gear teeth 86a. A drive socket 86d is formed on each of the opposite ends of articulation drive gear 86, sockets 86d each being configured as a Torx socket or other suitable configuration for engagement with a driving instrument to rotate articulation drive gear 86, as will be described.

Figure 12B:
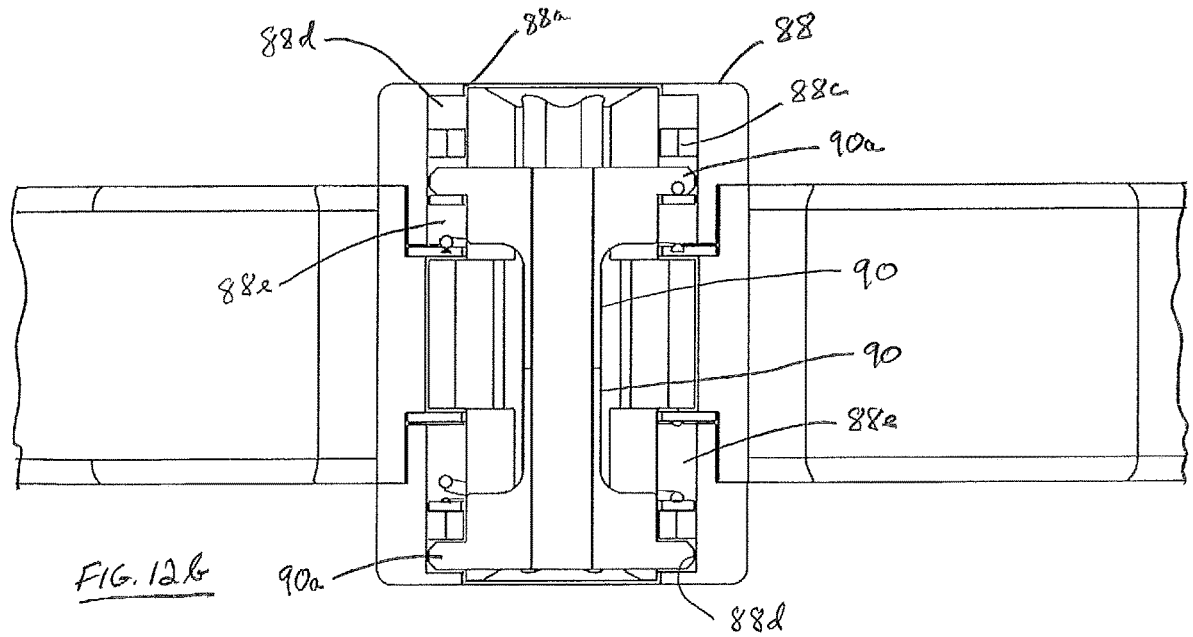
FIGS. 12a and 12b are cross-sectional views of the retractor arm as seen along viewing line XII-XII of FIG. 3 showing movement of inner components of the articulation drive mechanism during actuation.
Figure 12A:
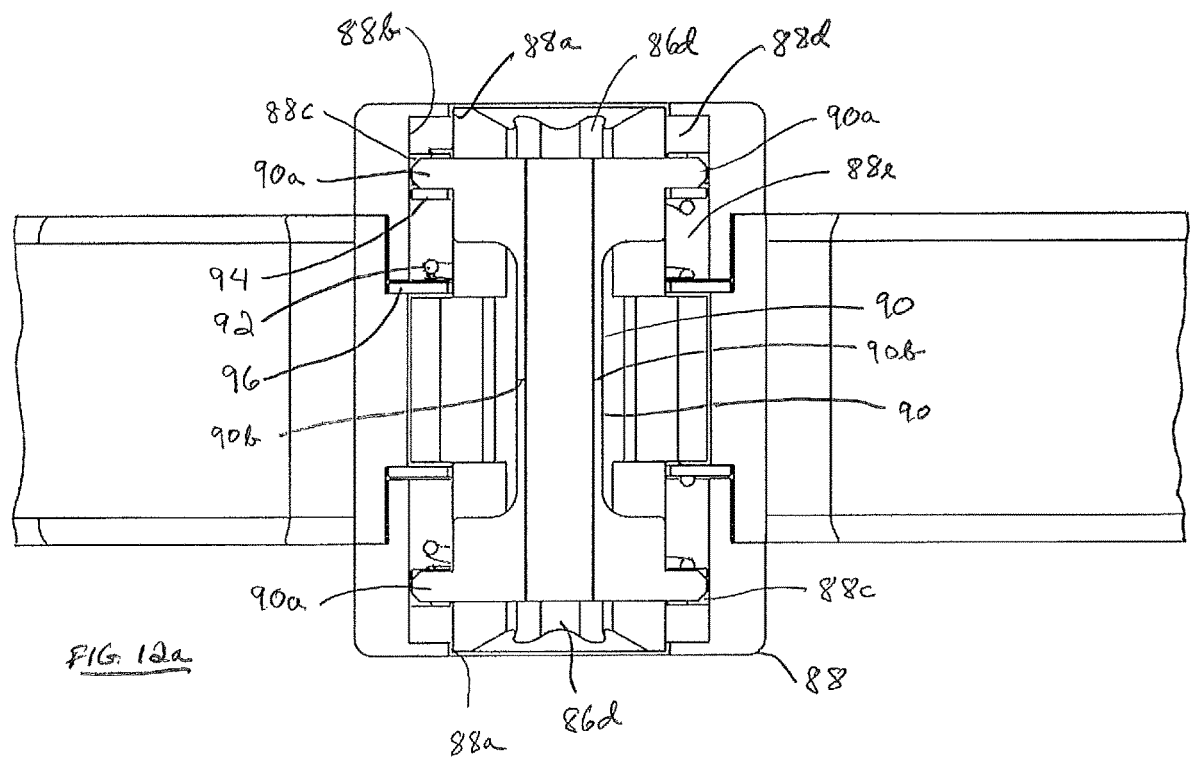

Referring also now to FIGS. 12a and 12b, a cap 88 closes the top and bottom of each container opening 74h, each cap 88 being identical. Each cap 88 is suitably affixed to blade arm container 86, such as by welding. Cap 88 has an opening 88a extending therethrough to expose drive sockets 86d of articulation drive gear 86 and an interior cavity 88b communicating with cap opening 88a. Cavity 88b has a diameter greater than the diameter of opening 88a. A ring of recesses 88c is formed about an interior circumference of cap 88 within interior cavity 88b, recesses 88c being in communication with cap opening 88a and dividing cavity 88b into an upper interior cavity 88d and a lower interior cavity 88e. Further supported within container opening 74h on each side of gear teeth 86a are spring-loaded upper and lower push keys 90, each having a pair of oppositely projecting wings 90a. Wings 90a are sized and configured to be selectively moved into and out from respective recesses 88b of cap 88. Wings 90a are also sized and configured to slide within opposing slots 86b of articulation drive gear 86. A compression spring 92 is captured between a pair of washers 94 and 96 on each side of gear teeth 86a. Each washer 94 contacts respective wings 90a and each washer 96 contacts a respective side surface of gear teeth 86a. A stud key 98 extends through and couples both push keys 90 such that rotation of either upper or lower key 90 will rotate the other key. The facing ends 90b of each key 90 are placed in contact with each other, as shown in FIG. 12a.

In the normally biased position as depicted in FIG. 12a, wings 90a of each push key 90 are disposed within respective recesses 88b of caps 88 with wings 90a of upper key 90 being located in slots 86b of articulation drive gear 86 and wings 90a of lower key 90 being in slots 86c. In such position rotation of articulation drive gear 86 is prevented. Upon introduction of a Torx tool (not shown) or other suitable tool into cap opening 88a of one of caps 88, such as the upper cap 88, and into the adjacent socket drive 86d of articulation drive gear 86, upper push key 90 is urged downwardly toward gear teeth 86a against the bias force of spring 92 causing wings 90a of upper key 90 to move out from cap recesses 88b. Upon such movement wings 90a of upper key 90 will move down into lower interior cavity 88e while lower key 90 will also be pushed downwardly separating keys 90a from lower recesses 88b and into upper interior cavity 88d of opposite lower cap 88, as shown in FIG. 12b. With wings 90a of each key 90 slidably remaining in respective slots 86b and 86c of articulation drive gear 86 during such movement, rotation of the drive tool in drive socket 86d will rotate articulation drive gear 86 and hence articulate blade receptacle 76 through the intermeshing of gear teeth 86a and blade receptacle gear teeth 76f, as described hereinabove. It should be appreciated that blade arm assembly 30 is reversible in the sense that it may be inverted and used in retractor arm 16, with opposite drive socket 86d facing upwardly so as to provide the ability to actuate the articulation drive mechanism 79 from above during surgery.

Figure 13:
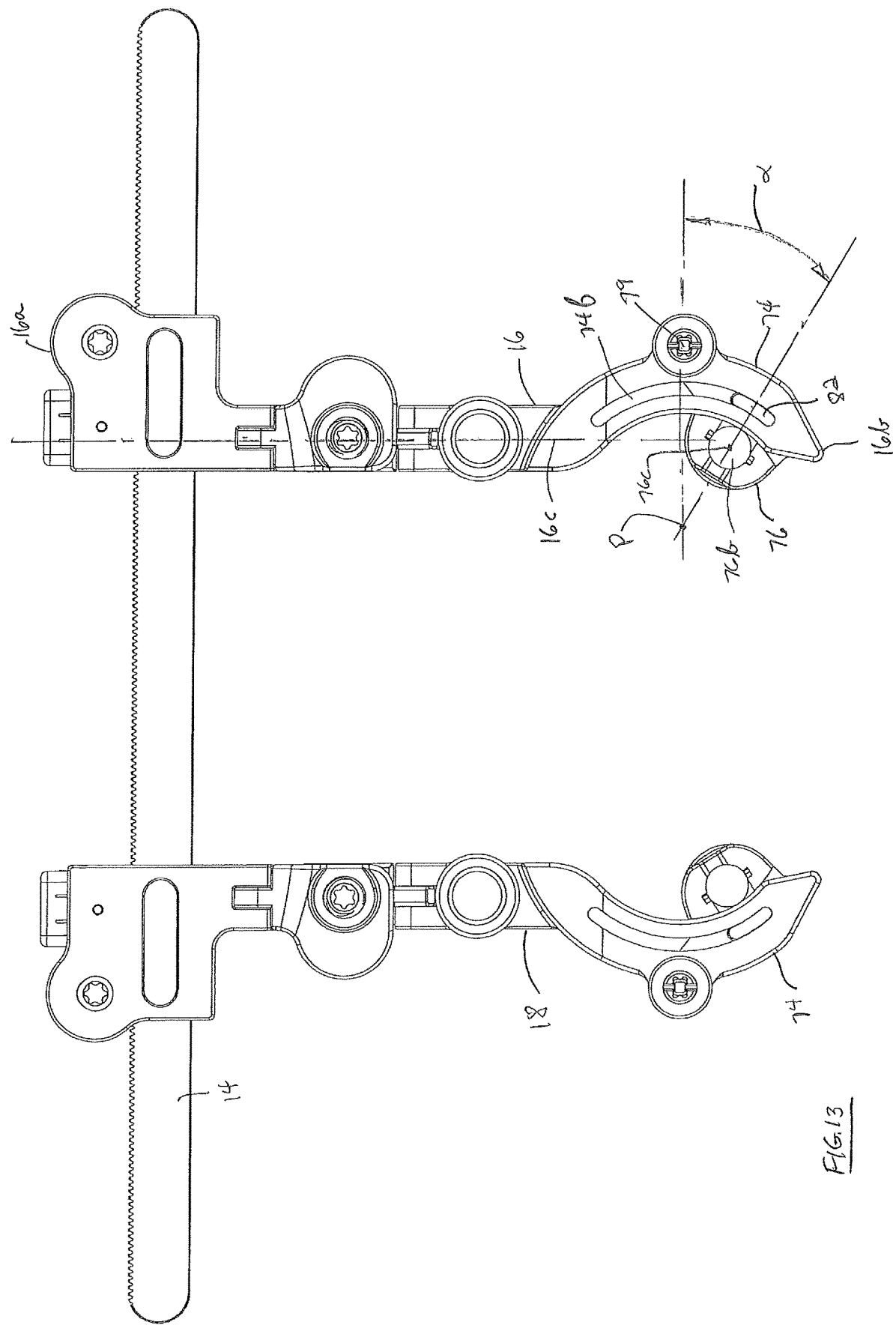
FIG. 13 is a further top plan view of the retractor view of FIG. 3 illustrating the articulation of the blade receptacle of the retractor arm to its distal most position about an articulation point, P.

Referring now to FIG. 13 and to FIG. 3, the innovative articulation aspect of the blade receptacle 76 is illustrated. As shown in FIG. 3 previously described, blade receptacle 76 is positioned with arc key 82 being generally centrally located in track 74f. Upon rotation of articulation gear 86 via articulation drive mechanism 79 as described hereinabove, blade receptacle 76 is articulated from the position of FIG. 3 to a position shown in FIG. 13. Blade receptacle 76 articulates about an articulation point, P through an angle, α with arc key 82 sliding along track 74f to its most distal position. Articulation point, P lies at a location spaced from and not on arm 16. In a particular arrangement, point, P is located transverse to arm axis 16c and between distal ends 16b and 18b respectively of retractor arms 16 and 18. Rotation of articulation gear 86 in the opposite direction will articulate blade receptacle 76 through an opposite angle, α with arc key 82 being moved to its most proximal position. Such articulation of blade receptacle 76 establishes a sixth degree of freedom of movement of a blade 20 attached to blade receptacle 76 relative to rack 14. It should be appreciated that the angle of articulation of blade receptacle 76 may be different in the distal and proximal directions.

Figure 14:
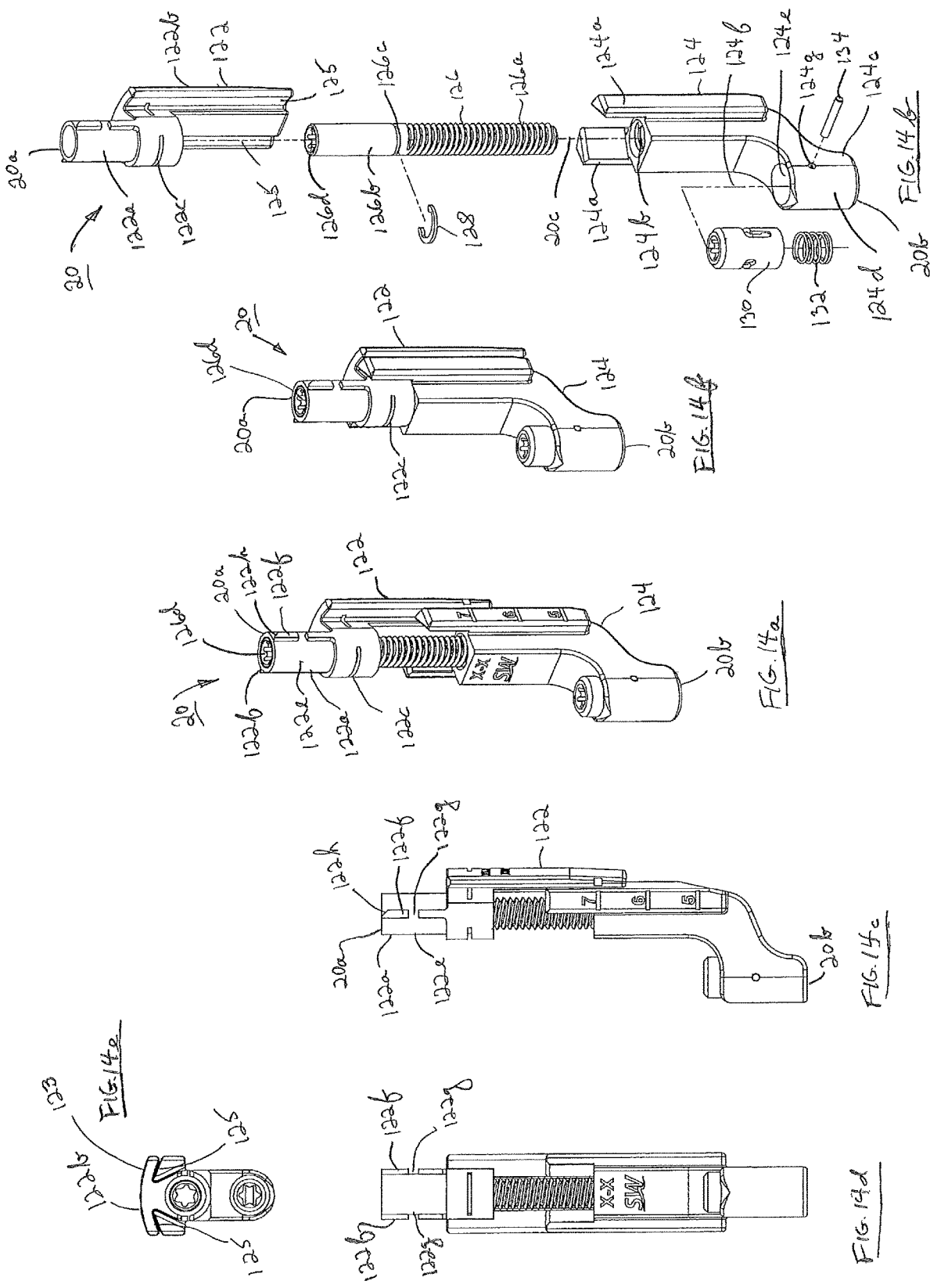

Turning now to FIGS. 14a-f, details of blade 20 are described. With blade 22 being identical to blade 20, details of only blade 20 are provided. Blade 20 is particularly configured for polyaxial attachment to a head of a pedicle screw prior to attachment of an articulatable yoke having a U-shaped slot for receipt of a fixation rod. This is the arrangement shown in FIG. 1. Blade 20 has a proximal end 20a and a distal end 20b. Blade 20 comprises a proximal blade 122 and a distal blade 124 movably attached by a threaded drive mechanism 126 as illustrated in FIG. 14b. Proximal end 20a of blade 20 is included on proximal blade 122 and defines an arm attachment 122a. Proximal blade 122 includes a blade extent 122b that extends between blade proximal end 20a and distal end 20b. Blade extent 122b in one arrangement comprises a curved outer convex surface 123, as seen in FIG. 14e. Concave surfaces 125 are included on the interior surface of blade extent 122b for slidable receipt with rails 124a on distal blade 124 during adjustment of the length of proximal blade 122 and distal blade 124 along blade axis 20c. Threaded drive mechanism 126 includes a threaded distal end 126a threadably received in threaded opening 124b of distal blade 124. Proximal end 126b of threaded drive mechanism 126 includes a circumferential recess 126c for receipt of a locking clip 128. Locking clip 128 is received in recess 126c through a slot 122c formed through proximal end 20a of proximal blade 122. Upon attachment of locking clip 128 within recess 126c threaded drive mechanism 126 may move rotatably but not axially relative to proximal blade 122. Proximal end 126b of threaded drive mechanism 126 further includes a drive socket 126d configured as a Torx socket or other suitable configuration for engagement with a driving instrument to rotate threaded drive mechanism 126. Rotation of threaded drive mechanism 126 causes distal blade 124 to move axially along axis 20c relative to proximal blade 122 via the threaded connection between threaded distal end 126a and threaded opening 124b to thereby allow adjustment of the length of blade 20. Such length adjustment establishes a seventh degree of freedom of movement of a blade 20 relative to rack 14. Full expansion of the length of blade 20 is shown in FIG. 14a while full contraction is shown in FIG. 14f.

Referring now particularly to FIGS. 14a and c, further details of the arm attachment 122a are explained. Arm attachment 122a comprises a generally cylindrical portion 122*e* that is sized and configured to be received within blade receptacle opening 76*b*, as described above. A pair of arm locking keys 122*f* projects oppositely radially outwardly from generally cylindrical portion 122*e*. Locking keys 122*f* are sized and configured to be received within respective opposed channels 76*d* of blade receptacle 76. Each locking key 122*f* is interrupted by a locking groove 122*g*, each locking groove 122*g* being sized and configured to receive therewithin a respective locking surface 78*c* of blade receptacle 76. The proximal end of each locking key 122*f* comprises an inclined cam surface 122*h*. Upon introduction of generally cylindrical portion 122*e* into blade receptacle opening 76*b* and locking keys 122*f* into respective blade receptacle channels 76*d*, cam surfaces 122*h* engage the underside of respective locking surfaces 78*c* and move frame 78*a* within slot 76*g* resiliently against the bias of springs 80 toward blade arm 74. Locking surfaces 78*c* on frame 78*a* are thereby moved out from interference with channels 76*d*, allowing locking keys 122*f* to move further within channels 76*d* until locking grooves 122*g* are in juxtaposition with locking surfaces 78*c*. At such point, locking surfaces 78*c* will snap into the locking grooves 122*g* under the bias force of springs 80 thereby releasably attaching blade 20 to blade receptacle 76. To release blade 20, button surface 78*e* of blade lock button 78 is manually depressed toward receptacle body 76*a* to overcome the bias force of springs 80 and move locking surfaces 78*c* out from grooves 122*g*, thereby allowing withdrawal of generally cylindrical portion 122*e* from blade receptacle opening 76*b* and release of blade 20 from blade receptacle 76.

Referring again to FIG. 14*b*, distal end 20*b* of blade 20 defines a screw attachment 124*c* for connection to modular pedicle screw 12 that is attached during surgery to a pedicle of a spine of a patient. Screw attachment 124*c* comprises a screw attachment member 124*d* projecting outwardly transversely from distal end 20*b* of distal blade 124 and toward blade 22. Screw attachment member 124*d* has a generally cylindrical opening 124*e* extending therethrough, opening 124*e* defining an opening axis 124*f*. Screw attachment member opening axis 124*f* is offset and generally parallel to blade axis 20*c*. A retainer 130 and a spring 132 are contained within opening 124*e* of screw attachment member 124*d*, retainer 130 being movably supported by a pin 134 extending into a hole 124*g* extending through screw attachment member 124*d*. Further details of these elements are described with reference to FIGS. 15-18.

Figure 15:
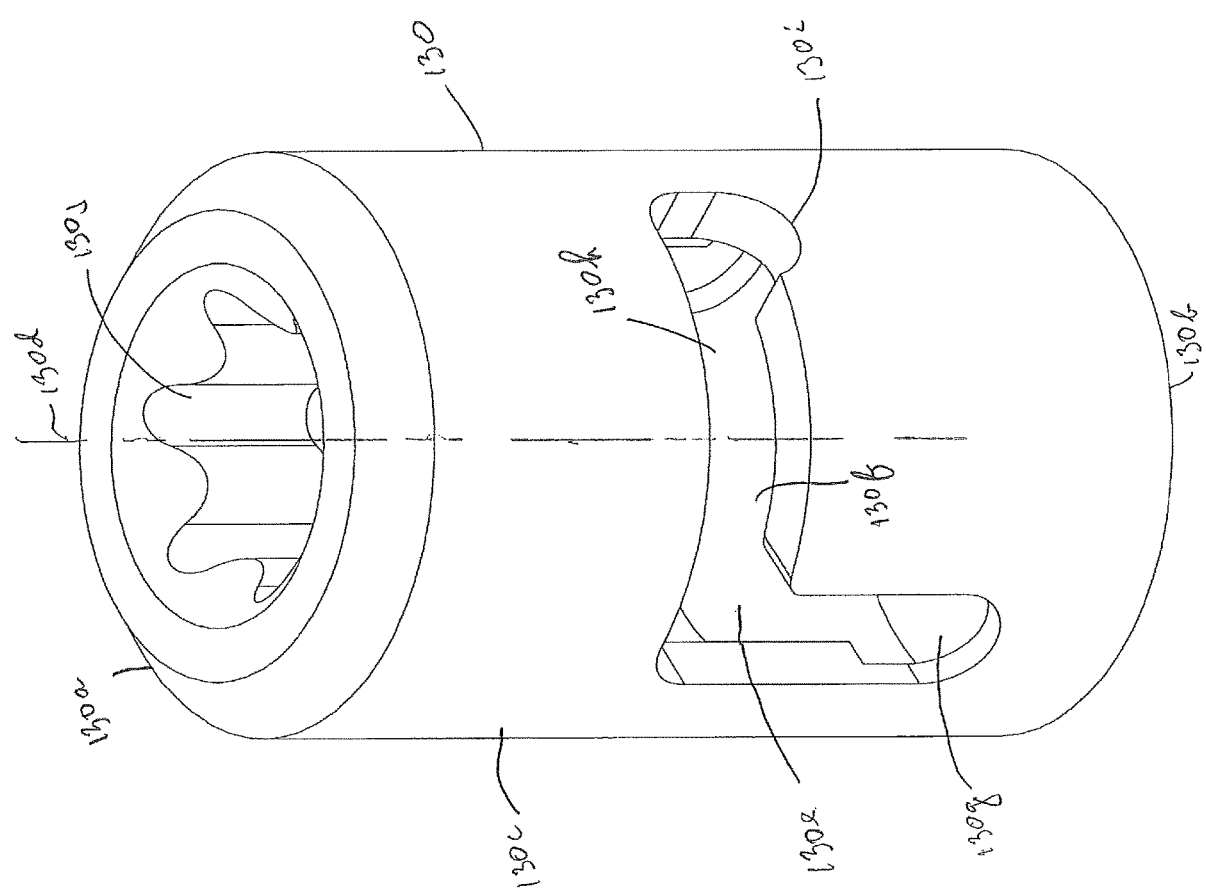
FIG. 15 is a top perspective view of a retainer for holding a head of a bone screw in the distal end of the retractor blade of the retractor arrangement of FIG. 1.

As illustrated in FIG. 15, retainer 130 comprises a proximal end 130*a*, a distal end 130*b* and a generally cylindrical outer surface 130*c* extending between proximal end 130*a* and distal end 130*b* and defining a retainer axis 130*d*. Retainer 130 has a hollow interior 130*e* open at distal end 130*b* and closed at proximal end 130*a*, hollow interior 130*e* being sized and configured to receive the head 12*a* of bone screw 12, as will be described. Retainer 130 has a slot 130*f* extending through outer surface 130*c* and into hollow interior 130*e*, slot 130*f* having a first axial portion 130*g* extending axially along retainer axis 130*d* and a second radial portion 130*h* extending partially circumferentially around cylindrical retainer 130. Radial portion 130*h* terminates in a recess 130*i* which provides a detent for releasably maintaining pin 132 in a temporary fixed position. A similar second slot 130*f* may be formed diametrically opposite slot 130*f*. Closed proximal end 130*a* of retainer 130 comprises a tool connection 130*j* for receipt of a tool to impart axial and rotational movement to retainer 130, tool connection comprising drive socket configured as a Torx socket or other suitable configuration for engagement with a driving instrument to rotate and apply an axial force to retainer 130.

Referring to FIG. 16, spring 132 is contained within hollow interior 130*f*, wherein spring 132 is supported on pin 134, pin 134 being affixed to screw attachment member 124*d* by press fit or other suitable attachment structure. In this position, retainer 130 is supported within screw attachment member opening 124*e* with pin 132 being disposed at the bottom of first axial portion 130*g* of slot 130*e* and spring 132 biasing retainer 130 upwardly. In this first axial position of retainer 130, ingress of bone head 12*a* is permitted through an entrance port 124*h* formed at the rearward junction 124*i* of screw attachment member 124*d* and lower blade 124, as shown in FIG. 17. Entrance port 124*h* communicates with screw attachment member opening 124*e* and allows entrance of bone screw head 12*a* into opening 124*e* in a direction transverse to axis 124*f* of screw attachment member opening 124*e*. As illustrated in FIG. 17, the distalmost opening 124*i* of entrance port 124*h* is dimensioned to be larger than a diameter of neck 12*c* between screw head 12*a* and threaded shaft 12*d* of bone screw 12 but smaller more than the diameter of screw head 12*a*. Additionally, the inner surface of entrance port 124*h* on both sides of distalmost opening 124*i* is formed to have a partially spherical surface to allow polyaxial movement of head 12*a* within screw head attachment 124*d*.

Upon introduction of bone screw head 12*a* into opening 124*e* through entrance port 124*h*, application of an axial force through tool connection 130*j* by a suitable tool moves retainer 130 against the bias force of spring 132 from its first axial position of FIG. 16 to a second axial position as shown in FIGS. 17 and 18. In the second position retainer distal end 130*b* partially covers bone screw head 12*a* thereby blocking egress of head 12*a*. During such axial movement of retainer 130 pin 134 is thus moved relatively upwardly in axial slot portion 130*g* to a location in alignment with radial slot portion 130*h*. Application of a radial force through tool connection 130*j* by the suitable tool rotates retainer 130 and thus moves pin 132 radially within radial slot portion 130*h* to a third position until pin 134 is disposed in the detent provided by slot recess 130*i*. As such, bone screw 12 is temporarily held in position in screw attachment member 124*d* at the distal end of blade 20. Bone screw 12 may be released from screw attachment member 124*d* upon application of an opposite radial force applied through tool connection 130*j* thereby radially moving pin 134 to a position in alignment with axial slot portion 130*g*, whereby spring 132 will apply a bias force to axially move retainer 130 proximally such that retainer distal end 130*b* does not cover bone screw head 12*a*, thereby allowing egress of bone screw head 12*a* out from port entrance 124*h*.

Turning now to FIGS. 19 and 20 the attachment of blade 20 to retractor arm 16 via blade receptacle 76 and the articulation of blade 20 relative to blade arm 74 are described. Blade 20 is releasably attached to blade receptacle 76 upon insertion of blade arm attachment 122*a* into blade receptacle opening 76*b*, as described hereinabove. Upon such attachment of blade 20, blade axis 20*c* is aligned substantially coaxially with receptacle blade opening axis 76*c* with blade axis 20*c* projecting generally transversely relative to rack axis 14*a* and to arm axis 16*c*. Substantially coaxially aligned axes 20*c* and 76*c* are offset from and substantially parallel to screw attachment member opening axis 124*f*. Articulation point, P, in a particular arrangement, is aligned substantially coaxially with screw attachment member opening axis 124*f*. As such, upon actuation of articulation drive mechanism 79 by a suitable drive tool, blade 20 effectively articulates about bone screw 12 attached to screw attachment member 124d. FIG. 19 shows articulation of blade 20 through angle, α to the distalmost position while FIG. 20 shows articulation of blade 20 through angle, α to the proximal most position.

Having described the embodiment of the subject screw-based retractor 10 that has applicability with modular pedicle screws 12, attention is now directed to FIGS. 21-25 which illustrate a further embodiment of a screw-based retractor 200 that is applicable for use with a traditional polyaxial pedicle screw after threaded installation into a pedicle of a spine, or with a modular pedicle screw after a yoke is attached to the head of the pedicle screw subsequent to threaded installation into a pedicle. Inasmuch as many of the components of retractor 200 and previously described retractor 10 are the same, like reference numerals in FIGS. 21-25 are used to designate corresponding parts in previous figures. Indeed, all of the components of retractor 200 are the same as retractor 10, except for blades 220 and 222, which are specifically configured to attach to a yoke of a polyaxial pedicle screw 212. Blades 220 and 222 are substantially identical and, as such, only the details of the blade 220 will be described, it being understood that such description equally applies to blade 222.

As shown in FIG. 21, polyaxial pedicle screw 212 comprises an elongate shaft 214 threaded at one end and a yoke 216 having a U-shaped slot 218 for receiving a fixation rod during surgery. Yoke 216 may be pre-assembled to the head of screw 212 before surgery in a traditional manner to allow articulating movement of the yoke 216 relative to the threaded shaft 214, or yoke 216 may be modular and attached during surgery after threaded shaft 214 is installed in a pedicle. As shown in FIG. 22, blade 220 comprises a screw attachment 226 projecting outwardly transversely from the distal end of blade 220 toward opposing blade 222.

Turning now to FIGS. 23a-e, details of blade 220 are described. With blade 222 being identical to blade 220, details of only blade 220 are provided. Blade 220 has a proximal end 220a a distal end 220b. Blade 220 comprises a proximal blade 122 and a distal blade 224 movably attached by a threaded drive mechanism 126 as illustrated in FIG. 23b. Proximal end 220a of blade 220 is included on proximal blade 122 and defines an arm attachment 122a. Proximal blade 122 includes a blade extent 122b that extends between blade proximal end 220a and distal end 220b. Threaded drive mechanism 126 is rotatably attached to proximal blade 122 by locking clip 128. Proximal blade 122, threaded drive mechanism 126 and locking clip 128 are the same construction as proximal blade 122, threaded drive mechanism 126 and locking clip 128 of retractor 10, the details of which are described hereinabove. Full expansion of the length of blade 220 is shown in FIG. 23a while full contraction is shown in FIG. 23e. Distal end 220b of distal blade 224 includes screw attachment 226. Screw attachment 226 comprises a screw attachment member 228 which is particularly in the form of a cylindrical post projecting outwardly transversely from the distal end 220b of distal blade 224. Post 228 comprises a flange 228a at the free end thereof, flange 228a extending transversely relative to post axis 228b and outwardly beyond an exterior surface 228c of post 228. The opposite end of post 228 is suitably attached, such as by welding, to distal end 220b of distal blade 224. The cylindrical exterior surface 228c of post 228 has a diameter of size to be received in U-shaped slot 218 of yoke 216. Post 228 may be releasably secured to yoke 216 by a suitable fixation element, such as a set screw 230 shown in FIG. 21 to hold blade 220 and pedicle screw 214 together during use of retractor 200 in compression, distraction and/or retraction procedures. Set screw 230 may be threaded into yoke 216 without full tightening so as to allow for limited polyaxial mobility of pedicle screw 214 while attached to retractor blade 220. Upon completion of desired distraction/retraction, blades 220 and 222, and hence retractor 200 are separated from pedicle screws 214 by removal of set screws 230.

Referring now to FIGS. 24 and 25, the attachment of blade 20 to retractor arm 16 via blade receptacle 76 and the articulation of blade 20 relative to blade arm 74 are described. Blade 220 is releasably attached to blade receptacle 76 upon insertion of blade arm attachment 122a into blade receptacle opening 76b, as described hereinabove. Upon such attachment, blade axis 20c is aligned substantially coaxially with receptacle blade opening axis 76c. Articulation point, P lies on post axis 228b spaced from and not located on retractor arm 16. As such articulation point P also lies within yoke 216. Therefore, upon actuation of articulation drive mechanism 79 by a suitable drive tool, blade 220 effectively articulates about bone screw 214 attached to post 228. FIG. 24 shows articulation of blade 220 through angle, α to the distalmost position while FIG. 25 shows articulation of blade 220 through angle, α to the proximal most position.

Having described screw-based retractor embodiments 10 and 200 herein, it should be appreciated that such retractors may be used for distracting and compressing vertebral bodies and retracting soft tissue. The retractor incorporates several features to easily connect to the head of a pedicle screw (retractor 10) or to the yoke of a pedicle screw (retractor 200), providing up to seven degrees of freedom to facilitate the surgical approach and patient anatomy. At four different locations on each retractor arm 16, 18, a male driver may be used to actuate individual features, which isolates individual degrees of freedom. The driver may be used to distract or compress the arms 16, 18 along rack 14 (drive socket 36a), pivot or toe the arms 16, 18 up to 150 bilaterally (drive socket 62d), articulate the blades (drive mechanism 79) through an angle, α up to 200 proximally and 20° distally (for a total articulation range of up to 400), and expand or contract the blades to a desired length (drive socket 126d). The expandable blades may be provided in lengths of 40-60 mm, 50-80 mm, and 80-120 mm sizes, although other suitable lengths may be used. Additionally, each retractor arm comprises a swivel joint whereby the blade arm with an attached blade may freely swivel about a swivel axis transverse to the axis of each retractor arm. Two separate hinges (at pins 56 and 66) allow for additional degrees movement of the segments that form the individual arms 16, 18. Both arms 16 include components of identical structure, making them cost effective for manufacturability and ease of use.

In use a retractor set is accompanied by a rack 14, a pair of retractor arms 16, 18 and sets of modular expandable blades 20, 22 and 220, 222, ranging in adjustable lengths as noted above. Each blade pairs screw-attaching structure to an arcing blade (curved blade extent 122b) that aids in the retraction of adjacent soft tissue. The curved blade extents maintain the ability to block soft tissue close to the screw connection even. One series of blades attaches solely to the screw head of a modular pedicle screw (retractor 10), while another series is locked into an articulating yoke of a polyaxial pedicle screw (retractor 200). The blades 20, 22 and 220, 222 automatically snap into the retractor blade receptacle 76, located in a subassembly of the arms 16, 18.

To remove the blades, the user depresses an accessible blade lock button 78 while pulling the blade from the receptacle 76.

A particularly desirable feature of the subject screw-based retractor (10, 200) is the addition of articulating blades to allow more degrees of freedom of movement, whereby the user may be allowed to avoid infringing bone structures or imperfectly placed screws. Additionally, the articulation may be utilized to target and retract soft tissue much more effectively in circumstances where tissue creep is not abundant but closing in on a surgical sight at unique angles.

In another aspect, the bilateral pivotal or toeing motion of the arms paired with the expansion of the blades, allows for the screw-based retractor (10, 200) to accommodate the curvature of the spine where screws are placed accordingly during surgery. This helps to minimize the potential of the fixed rack 14 from digging into a patient, while still empowering the user to have a multi-level retraction system.

In a further aspect, the versatility of the modular expandable blades (20,22 and 220, 222) allows the user to alter his/her procedure as necessary. At times, the intervertebral disc space may be distracted prior to the full assembly of the modular screw, while at other times it will be distracted after the full assembly of the modular screw.

In yet a further aspect, the relatively large curved surface 122*b* on the rear of the blades and the available articulation of the blades about the screw head allow for soft tissue retraction simultaneously with disc space distraction and further enforces the versatility of the retractor.

In yet another aspect, releasable retention of the head of a pedicle screw in the screw attachment member of a blade 20, 22 provides the user with enhanced security that the pedicle screw will be maintained in attachment to the blade during the compression, distraction and/or retraction procedures.

The subject retractor (10, 200) may be used laterally or midline since there are features to keep it out of the way and close to the patient during use. The surgeons will thus have more space to work when using the subject retractors (10, 200).

It should therefore be understood that while certain embodiments of the invention have been presented herein, various changes, modifications and further applications may be made without departing from the spirit of the invention and the scope of the appended claims. For example, supplementary third and fourth retractor arms with attached blades may be incorporated to assist in the retraction of adjacent tissue. Such supplementary arms and blades may incorporate certain features described herein or employ conventional retractor arm and blade structure. One example of such further embodiment is shown in FIG. 26, which is directed to a screw-based retractor 300 that has applicability with modular pedicle screws 12, similar to screw-based retractor 10. Inasmuch as some of the components of retractor 300 and previously described retractor 10 are the same, like reference numerals are used to designate corresponding parts in previous figures.

Retractor 300 comprises an elongate rack 14 having a longitudinal rack axis 14*a*, a pair of spaced arms 316 and 318, each of which are slidably translatable along rack 14, each arm 316, 318 comprising a respective retractor blade 320 and 322 releasably attached thereto. Briefly, each of retractor arms 316, 318 comprises a plurality of swivel joint links with each link having a mechanism similar to swivel joint link 28, described above, to allow blades 320, 322 supported at the distal ends of respective retractor arms 316, 318 to be moved in plural incrementally discrete positions with each such discrete position being selectively lockable. Further, each retractor blade 320, 322 is of fixed length with an arm attachment at the proximal end that is configured for releasable attachment to respective arms 316, 318 of retractor 300. Since the arm attachment of each fixed blade 320, 322, as will be described, is identical to the arm attachment of retractor blades 20, 22, blades 320, 322 and blades 20,22 may be used interchangeably in screw-based retractors 10 and 300.

In addition, retractor 300 may include a supplementary third retractor arm 400 with attached blade 402, which would further assist in the retraction of adjacent tissue. Third arm 400 may be movably attached to rack 14 by a housing 432 having an opening 432*a* extending therethrough for slidable receipt of rack 14 along axis 14*a*. Housing 432 comprises an upper portion 434 having an opening 434*a* extending therethrough for slidable receipt of third arm 400 along axis 400*a* in a direction substantially transverse to axis 14*a*. Housing upper portion 434 may include a mechanism that in cooperation with housing 432 provides for pivoting motion of blade 402 about an axis above and substantially parallel to axis 14*a*. Blade 402 may have a generally cylindrical post 404 at its proximal end which may be attached to arm 400 by a spring-biased release mechanism 406. Blade 402 may have a blade extent 408 of fixed length, of fixedly adjustable length, or configured to be automatically self-adjusting in a manner as described in U.S. Pat. No. 3,749,088, issued to William Kohlmann on Jul. 31, 1973, the entire contents of which are incorporated by reference herein.

The components of each retractor arm 316 and 318 are substantially identical and, as such, only the details of the components of retractor arm 318 will be described except as noted, it being understood that such description applies equally to the components of retractor arm 316. Turning now to FIG. 27, further details of the components of retractor arm 318 are described. As some of the components of arms 316, 318 and arms 16, 18 described above are the same, like reference numerals are used to designate those components in arm 318 that correspond to like components in arms 18. Retractor arm 318 is multi-faceted and defines an arm axis 318*c* extending generally transversely relative to rack axis 14*a*. Arm 318 has a proximal end 318*a* and a distal end 318*b*. Proximal end 318*a* slidably attaches to rack 14 and distal end 318*b* is releasably attachable to blade 322. Arm 318 comprises a retraction control unit 324, a first swivel joint link 28, a second swivel joint link 325, a third swivel joint link 326, and a blade arm assembly 30. Retraction control unit 324 defines a proximal portion slidably attached to rack 14 at the proximal end 318*a* of arm 318 while blade arm assembly 30 defines a distal portion releasably attachable at the distal end 318*b* of arm 318 to blade 322, as shown in FIG. 26.

The components forming first swivel joint link 28 as illustrated in FIG. 27 are substantially identical to swivel joint link 28 in retractor arms 16, 18 and function in the same manner. First swivel joint link 28 in arm 318 differs from arms 16, 18 in that first swivel joint link 28 in arm 318 comprises two bodies 64. The first body 64 is directly coupled to a first connector 74*b* of blade arm assembly 30 in the same manner as in retractor arm 16, 18 and defines a swivel axis 28*a*, which in a particular arrangement extends transversely to rack axis 14*a*. The second body 64 of first swivel link 28 is directly coupled to and forms a component of third swivel joint link 326. Second body 64 likewise comprises an upper ring 64*a*, a lower ring 64*b*, a generally circular opening 64*c* extending therethrough and a generally circular recessed floor 64*d*. Third swivel joint link 326 is further formed by a hex button 68, a spring 70, and a second connector 74*b* having an opening 74*c* with a shaped inner circumference 74*d*. Second connector 74*b* is supported by another portion of retractor arm 318, namely short link 58. Like swivel joint link 28, inner circumference 74*d* of third swivel joint link 326 is configured in a particular arrangement to have a 12-point star feature for selective engagement with the hex configuration of hex button lower portion 68*b*, as seen in FIG. 27. Opening 74*c* of third swivel link 326 defines a third swivel axis 326*a*, which in a particular arrangement extends generally parallel to rack axis 14*a*.

Short link 58 is coupled to a further portion of retractor arm 318, namely link member 46. Short link 58 and link member 46 function in cooperation with a pivot stud 62 in substantially the same manner as pivot link 26 described hereinabove with reference to arm 316 of retractor 10 to provide a pivot motion of blade 322. Unlike retractor arm 316, however, link member 46 comprises a third connector 74*b* that forms a component of second swivel joint link 325. Second swivel joint link 325 is further formed by a hex button 68, a spring 70, and connector 74*b* having an opening 74*c* with a shaped inner circumference 74*d*. Second swivel joint link 325 comprises a third body 64 extending transversely from retraction control unit 324. Third body 64 likewise comprises an upper ring 64*a*, a lower ring 64*b*, a generally circular opening 64*c* extending therethrough and a generally circular recessed floor 64*d*. Like swivel joint link 28, inner circumference 74*d* of second swivel joint link 325 is configured in a particular arrangement to have a 12-point star feature for selective engagement with the hex configuration of hex button lower portion 68*b*, as seen in FIG. 27. Opening 74*c* of second swivel link 325 defines a second swivel axis 325*a*, which in a particular arrangement extends generally parallel to rack axis 14*a*.

Other than third body 64, retraction control unit 324 is structured and functions substantially the same as retraction control unit 24 described above with respect to retractor arms 16, 18. While in retractor 300 both arms 316 and 318 may have the plurality of swivel joint links 28, 325 and 326 described herein, it should be appreciated that at least one of arms 316 or 318 may comprise such plurality of such links, each of which is configured to allow a respective blade 320 or 322 supported at the end of the distal end of such at least one arm to be moved in plural incrementally discrete positions with each such discrete position being selectively lockable, as described above.

Turning now to FIGS. 28, 28*a* and 29, further details of retractor blades 320, 322 are described. With blade 320 being identical to blade 322, details of only blade 322 are provided. Blade 322 is particularly configured for attachment to a head of a pedicle screw prior to attachment of an articulatable yoke having a U-shaped slot for receipt of a fixation rod. This is the arrangement shown in FIG. 26. Blade 322 has a proximal end 322*a* and a distal end 322*b* and a blade extent 322*c* extending therebetween Blade extent 322*c* in one arrangement comprises a curved outer convex surface 322*d*, as seen in FIG. 28*a* and a concave interior surface 322*e*, as seen in FIG. 29. Blade extent 322*c*, and indeed the entire blade 322 has a length of fixed dimension. Proximal end 322*a* of blade 322 defines an arm attachment 122*a* identical to arm attachment 122*a* described above with reference to FIGS. 14*a*-14*f*. Thus, arm attachment 122*a* comprises a cam surface 122*h* inclined at an angle relative to blade axis 322*f*, cam surface 122*h* being configured to move a portion of the arm 318 upon relative movement along said blade axis 322*f* against such arm portion, as described above. As seen in FIG. 28, as well as in FIG. 14*c*, cam surface 122*h* is planar. It should thus be appreciated that the retractor blade 322 may also be releasably attached to retractor arm 18 of retractor 10, while retractor blade 22 of retractor 10 may also be releasably attached to retractor arm 318 of retractor 300.

Distal end 322*b* of blade 322 defines a screw attachment 330 for connection to modular pedicle screw 12 that is inserted during surgery to a pedicle of a spine of a patient. Screw attachment 330 comprises an outer locking sleeve 332 fixedly attached to blade extent 322*c*. Outer locking sleeve 332 has a generally cylindrical opening 332*a* extending therethrough that defines an opening axis 332*b*. Screw attachment 330 includes a generally cylindrical retainer 334 rotatably supported within opening 332*a* of outer locking sleeve 332, retainer 334 having a closed proximal end 334*a* and an open distal end 334*b*. Retainer 334 is rotatable about opening axis 332*b* within outer locking sleeve opening 332*a* from a first position to a second position, as will be described. Retainer 334 supports a plurality of balls 336, balls 336 being movable upon rotation of retainer 334 from the first position allowing ingress of the head of a bone screw 12 to a second position preventing egress of the head of bone screw 12, as will be further described. Retainer 334 is supported for limited rotational movement within opening 332*a* of outer locking sleeve 332 by a pin 338. Pin 338 extends through an opening 332*c* extending through the wall of outer locking sleeve 332 and into a slot 334*c* formed into retainer 334, as seen in FIG. 28*a*. Slot 334*c* extends partially circumferentially around retainer 334 and in a particular arrangement, slot 334*a* extends 90° around retainer 334, thereby allowing retainer 334 to be rotated about a quarter turn relative to outer locking sleeve 332.

With further reference now to FIGS. 30, 31, 32*a*, 32*b*, 33*a* and 33*b* additional details of screw attachment 330 are described. FIGS. 30 and 31 illustrate the connection between blade 322 and bone screw 12. As shown in further detail in FIGS. 32*a* and 33*a*, outer locking sleeve 332 has an interior surface 332*d* that defines opening 332*a* extending through outer locking sleeve 332. Interior surface 332*d* comprises a plurality of circumferentially spaced shallow grooves 332*e* extending into interior surface 332*d*. In the particular arrangement shown, there are three grooves 332*e*, each spaced approximately 120° apart.

The open distal end 334*b* of retainer 334 has a counterbore forming an inner opening 334*d* defined by an inner surface 334*e*. Retainer 334 has an outer surface 334*f* that together with inner surface 334*e* defines a circumferential wall 334*g*. Circumferential wall 334*g* has a substantially uniform radial thickness and comprises a plurality of circumferentially spaced sockets 334*h* extending through circumferential wall 334*g* and communicating with inner opening 334*d*. Each socket 334*h* opens at the inner surface 334*e* in a dimension less than the diameter of each ball 336, such that only a portion of each ball 336 can extend into inner opening 334*d*. Each socket 334*h* is spaced circumferentially approximately the same as the spacing between grooves 332*e* of locking sleeve 332. In the particular arrangement shown, there are three sockets 334*h*, each spaced approximately 120° and each supporting a ball 336 as shown in FIG. 33*a*. Each ball 336 has a diameter greater than the thickness of circumferential wall 334*g* and is radially movable within a respective socket 334*h*. In a first position a portion of each ball 336 is movable radially outwardly beyond outer surface 334*f* of retainer 334, and in a second position a diametrically opposite portion of each ball 336 is movable radially inwardly into inner opening 334*d* of retainer 334. As will be described, balls 336 are movable upon rotation of retainer 334 relative to outer locking sleeve 332 from a first position allowing ingress of a head of bone screw 12 to a second position preventing egress of head of bone screw 12.

In use, FIGS. 32a and 33a show the outer locking sleeve 332 and retainer 334 in the first position. With each groove 332e of locking sleeve 332 being spaced circumferentially approximately the same as the spacing between sockets 334h of retainer 334, groves 332e and sockets 334h are alignably registered. As such, in this first position a portion of each ball 336 may freely extend radially outwardly beyond the outer surface 334f of retainer 334 and into a respective groove 332e with the diametrically opposite portion of each ball 336 lying within a respective socket 334h. Inner opening 334d of retainer 334 is therefore substantially unimpeded in this first position allowing ingress of a head 12a of bone screw 12. The depth of retainer inner opening 334d is configured to allow the maximum diameter of bone screw head 12a to lie more proximally in opening 334d than the location of balls 336, as illustrated in FIG. 32a.

Rotation of retainer 334 to the second position is shown in FIGS. 32b and 33b. With grooves 332e and sockets 334h being spaced approximately 120° apart, rotation of retainer 334 in a 90° angle as limited by the cooperation between pin 338 and retainer slot 334c as described above, will cause grooves 332e and sockets 334h to move out from registry. In this second position, a portion of each ball 336 extends into inner opening 334d of retainer 334 and the diametrically opposite portion of each ball is constrained by interior surface 332d of locking sleeve 332. The tangent points of the portion of balls 336 extending into retainer inner opening 334d define a retention diameter that is less than the maximum diameter of bone screw head 12a, as illustrated in FIG. 32b. With the maximum diameter of bone screw head 12a lying more proximally relative to the location of balls 336, and with outward radial movement of each ball 336 being constrained, a condition preventing egress of bone screw head 12a is established. Rotation of retainer 334 in the opposite direction back to the first position will allow separation of screw attachment 330, and thereby retractor blade 322, from head 12a of bone screw 12. Rotation of retainer 334 may be effected by a tool suitably engaged with a tool connection 340 formed in the closed proximal end 334a of retainer 332, as shown in FIG. 29.

Having described the embodiment of the screw-based retractor 300 that has applicability with modular pedicle screws 12, attention is now directed to FIG. 34 which illustrates yet a further embodiment of a screw-based retractor 500 that is applicable for use with a traditional polyaxial pedicle screw after threaded installation into a pedicle of a spine, or with a modular pedicle screw after a yoke is attached to the head of the pedicle screw subsequent to threaded installation into a pedicle. All of the components of retractor 500 are the same as the components of retractor 300, except for the retractor blades 520 and 522. As such, like reference numerals are used to designate corresponding parts. Blades 520 and 522 differ from blades 320 and 322 in that blades 520 and 522 are configured to attach to a yoke of a polyaxial pedicle screw 212, as described above.

Blades 520 and 522 are substantially identical and, as such, only the details of blade 522 will be described, it being understood that such description equally applies to blade 520. As shown in FIGS. 35-36, blade 522 has a proximal end 522a, a distal end 522b and a blade extent 522c extending therebetween Blade extent 322c in one arrangement comprises a curved outer convex surface 522d and a concave interior surface 522e. Blade extent 522c, and indeed the entire blade 522 has a length of fixed dimension. Proximal end 522a of blade 522 defines an arm attachment 122a identical to arm attachment 122a described above with reference to FIGS. 28-29. Thus, arm attachment 122a comprises a cam surface 122h inclined at an angle relative to blade axis 522f, cam surface 122h being configured to move a portion of the arm 318 upon relative movement against such arm portion, as described above.

Distal end 522b of blade 522 includes screw attachment 526. Screw attachment 526 is identical to screw attachment 226 and functions in the same manner as described above, with like reference numerals being are used to designate corresponding parts.

While the various embodiments have been illustrated and described in detail in the drawings and foregoing description, the same should be considered as illustrative and not restrictive in character. It is understood that only particular embodiments have been presented and that all changes, modifications and further applications that come within the spirit of the invention are desired to be protected.

What is claimed is:

1. A screw-based retractor, comprising:
an elongate rack having a rack axis;
a plurality of arms slidably supported for translational movement on said rack toward and away from each other, each arm having an arm axis and comprising a proximal portion slidably supported by said rack and a distal portion, each said arm axis extending generally transversely relative to said rack axis; and
a plurality of blades, each blade being supported by a respective arm at the distal portion thereof, said blades projecting generally transversely relative to said rack axis and to said arm axis, each of said blades having a proximal end defining an arm attachment in attachment with said distal portion of a respective arm, an opposing distal end defining a screw attachment, and a blade extent extending between said proximal end and said distal end;
at least one of said arms comprising a plurality of links each of which is configured to allow said blade supported at the end of the distal end of said at least one arm to be moved in plural incrementally discrete positions with each such discrete position being selectively lockable, each said link comprising a mechanism to allow movement of said at least one blade relative to said rack axis in said plural incrementally discrete positions, each of said link mechanisms comprising a component having a plurality of discrete engagement surfaces selectively engageable with one of a plurality of discrete complementary engagement surfaces on another portion of said at least one arm.

2. The screw-based retractor of claim 1, wherein said engagement surfaces of each said link component and said complementary engagement surfaces on said another portion of said at least one arm are selectively rotatably engageable.

3. The screw-based retractor of claim 2, wherein each said link component comprises a generally cylindrical button having a longitudinal axis, said plurality of engagements surfaces extending circumferentially about said longitudinal axis, and wherein said another portion of said at least one arm comprises an opening for receipt of said button, said opening having an inner surface comprising said plurality of complementary engaging surfaces extending circumferentially therearound.

4. The screw-based retractor of claim 3, wherein said button is axially movable along said longitudinal axis, wherein said button comprises a non-engagement region axially spaced from said plurality of engagement surfaces on said button, and wherein said button is movable axially from a first position wherein said button engagement surfaces are in engagement with said complementary engagement surfaces within the opening of said another portion of said at least one arm to a second position wherein said non-engagement region of said button is aligned with and not engaged with said complementary engagement surfaces, said another portion of said at least one arm portion being freely rotatable relative to the longitudinal axis of said button with said button in said second position.

5. The screw-based retractor of claim 4, wherein said button is normally biased in each said link in said first position wherein said engagement surfaces on said button are in a releasably locked position with the complementary engagement surfaces within the opening of said another portion of said at least arm.

6. The screw-based retractor of claim 5, wherein each said link includes a spring providing a surmountable bias force applied to said button to hold said button in said first position, said bias force being overcome by manual depression of said button from said first position to said second position.

7. The screw-based retractor of claim 6, wherein said engagement surfaces comprise six surfaces disposed about the circumference of said button in a hex configuration.

8. The screw-based retractor of claim 7, wherein said complementary engagement surfaces within the opening of said another portion of said at least arm are configured in a 12-point star arrangement for selective engagement with different engagement surfaces in the hex configuration of said button.

9. The screw-based retractor of claim 8, wherein said another portion of said at least one arm is said distal portion of said at least one arm, and wherein a first of said plurality of links is movably coupled to said distal portion of said at least one arm to allow joint movement of said distal portion of said at least one arm and said blade supported at the end of the distal end of said at least one arm relative to said rack axis.

10. The screw-based retractor of claim 9, wherein said longitudinal axis of said button of said first link is transverse to said rack axis.

11. The screw-based retractor of claim 9, wherein a second of said plurality of links is movably coupled to said at least one arm between said rack and said first link.

12. The screw-based retractor of claim 11, wherein a third of said plurality of links is movably coupled to said at least one arm between said first link and said second link.

13. The screw-based retractor of claim 1, wherein said plurality of arms comprises first and second arms movably spaced on said rack, wherein said screw-based retractor further comprises a third arm movably supported on said rack between said two arms, said third arm movably supporting a third retractor blade.

14. A screw-based retractor, comprising:
an elongate rack having a rack axis;
a plurality of arms slidably supported for translational movement on said rack toward and away from each other, each arm having an arm axis and comprising a proximal portion slidably supported by said rack and a distal portion, each said arm axis extending generally transversely relative to said rack axis; and
a plurality of blades, each blade being supported by a respective arm at the distal portion thereof, said blades projecting generally transversely relative to said rack axis and to said arm axis, each of said blades having a proximal end defining an arm attachment in attachment with said distal portion of a respective arm, an opposing distal end defining a screw attachment, and a blade extent extending between said proximal end and said distal end;
at least one of said arms comprising a plurality of links each of which is configured to allow said blade supported at the end of the distal end of said at least one arm to be moved in plural incrementally discrete positions with each such discrete position being selectively lockable,
wherein said at least one arm includes at its distal portion a blade receptacle movably attached to said distal portion in a manner to provide articulation of said blade receptacle in a curved path relative to said at least one arm about an articulation point spaced from and not located on said at least one arm.

15. A tissue retractor blade for releasable attachment to an arm of a screw-based retractor, comprising:
a proximal end, a distal end and a blade extent therebetween extending along a blade axis;
an arm attachment at the proximal end of said blade comprising a cam surface inclined at an angle relative to said blade axis, said cam surface being configured to move a portion of said arm of said retractor upon relative movement along said blade axis against said portion of said arm, said arm attachment including a generally cylindrical portion and a pair of substantially diametrically opposed projections extending radially outwardly from said generally cylindrical portion, each of said projections including a respective said cam surface, each of said projections being defined by a locking key extending axially along said generally cylindrical portion and separated by a groove, said respective cam surfaces being disposed at a proximal end of each locking key; and
a screw attachment at the distal end of said blade, said screw attachment being configured for releasable connection to a bone screw.

16. The tissue retractor blade of claim 15, wherein said cam surface is planar.

17. The tissue retractor blade of claim 15 wherein said blade extent has a length of fixed dimension.

18. The tissue retractor blade of claim 17, wherein said blade extent has an adjustable length.

19. The tissue retractor blade of claim 15, wherein said screw attachment is configured for releasable attachment to a head of a bone screw.

20. The tissue retractor blade of claim 15, wherein said screw attachment is configured for releasable attachment to a yoke of a polyaxial bone screw.

21. A tissue retractor blade for releasable attachment to an arm of a screw-based retractor, comprising:
a proximal end, a distal end and a blade extent therebetween extending along a blade axis;
an arm attachment at the proximal end of said blade configured for releasable attachment to said arm of said retractor; and
a screw attachment at the distal end of said blade for releasable attachment to a head of a bone screw, said screw attachment including an outer locking sleeve fixed relative to said blade extent and having an opening therethrough, said screw attachment including a retainer rotatably supported within said opening of said outer locking sleeve, said retainer comprising a circumferential wall having an outer surface and an inner surface, said inner surface defining an inner opening, said retainer supporting a plurality of balls in communication with said inner opening, said balls being movable upon rotation of said retainer from a first position allowing ingress of said head of said bone screw to a second position preventing egress of said head of said bone screw.

22. The tissue retractor of blade of claim 21, wherein said opening of said outer locking sleeve is generally cylindrical with the axis of said cylinder defining an opening axis, wherein said retainer is generally cylindrical and comprises a proximal end and a distal end, and wherein said retainer is rotatable about said opening axis during movement from said first position to said second position.

23. The tissue retractor blade of claim 22, wherein said circumferential wall of said retainer has a radial thickness, and wherein said retainer comprises a plurality of circumferentially spaced sockets extending through said circumferential wall and communicating with said inner opening of said retainer.

24. The tissue retractor blade of claim 23, wherein each ball is supported by said retainer in a respective socket, each ball having a diameter greater than the thickness of said circumferential wall of said retainer and being radially movable within a respective socket, such that a portion of each ball is movable radially beyond said outer surface of said retainer when said retainer is in said first position and a portion of each ball is movable radially into said inner opening of said retainer when said balls are in said second position.

25. The tissue retractor blade of claim 24, wherein an interior surface of said outer locking sleeve defines the opening through said outer locking sleeve, said interior surface comprising a plurality of circumferentially spaced grooves extending into said interior surface, each groove being spaced circumferentially approximately the same as the spacing between said sockets of said retainer such that upon rotation of said retainer within said opening of said outer locking sleeve, said sockets of said retainer alignably register with the grooves in the interior surface of said locking sleeve.

26. The tissue retractor blade of claim 25, wherein said retainer has a slot extending through said circumferential wall and into said inner opening, said retainer slot extending partially circumferentially around said cylinder.

27. The tissue retractor blade of claim 26, wherein said outer locking sleeve supports a pin received in said retainer slot, said pin being movable in said retainer slot during movement of said retainer from said first position to said position and limiting the angle of rotation of said retainer.

28. The tissue retractor blade of claim 27, wherein when said retainer is in the first position said sockets and grooves are aligned in registry such that a portion of each ball extends radially outwardly beyond said outer surface of said retainer and the diametrically opposite portion of said ball lies within a respective socket such that the inner opening of said retainer is substantially unimpeded to thereby allow ingress of the head of said bone screw.

29. The tissue retractor blade of claim 28, wherein when said retainer is in the second position said sockets and grooves are not aligned in registry such that a portion of each ball extends into said inner opening of said retainer and the diametrically opposite portion of said ball is constrained by the interior surface of said locking sleeve thereby preventing outward radial movement of such ball and establishing a condition to prevent egress of the head of said bone screw.

30. The tissue retractor blade of claim 22, wherein said proximal end of said retainer is closed and comprises a tool connection for receipt of a tool to impart rotational movement to said retainer.

* * * * *